(12) United States Patent
Kim et al.

(10) Patent No.: US 12,398,202 B2
(45) Date of Patent: *Aug. 26, 2025

(54) USE OF ITIH1 AS BIOMARKER FOR DETECTION OF INSULIN RESISTANCE IN DISEASES ACCOMPANIED BY IMPAIRED GLUCOSE TOLERANCE

(71) Applicant: APHARMA, Goyang-si (KR)

(72) Inventors: Sang Geon Kim, Seoul (KR); Yeonseok Chung, Seoul (KR); Tae Hyun Kim, Seoul (KR); Won Kim, Seoul (KR)

(73) Assignee: APHARMA, Goyang-si (KR)

( * ) Notice: Subject to any disclaimer, the term of this patent is extended or adjusted under 35 U.S.C. 154(b) by 846 days.

This patent is subject to a terminal disclaimer.

(21) Appl. No.: 17/774,076

(22) PCT Filed: Sep. 3, 2020

(86) PCT No.: PCT/KR2020/011814
§ 371 (c)(1),
(2) Date: May 3, 2022

(87) PCT Pub. No.: WO2021/045515
PCT Pub. Date: Mar. 11, 2021

(65) Prior Publication Data
US 2022/0411488 A1 Dec. 29, 2022

(30) Foreign Application Priority Data
Sep. 4, 2019 (KR) ........................ 10-2019-0109433

(51) Int. Cl.
*C07K 16/18* (2006.01)
*G01N 33/50* (2006.01)
(Continued)

(52) U.S. Cl.
CPC ......... *C07K 16/18* (2013.01); *G01N 33/5091* (2013.01); *G01N 33/563* (2013.01);
(Continued)

(58) Field of Classification Search
None
See application file for complete search history.

(56) References Cited

U.S. PATENT DOCUMENTS 9,651,563 B2    5/2017   Jacobs et al.

FOREIGN PATENT DOCUMENTS

| KR | 10-2009-0121842 A | 11/2009 |
|---|---|---|
| KR | 10-2013-0079951 A | 7/2013 |

(Continued)

OTHER PUBLICATIONS

International Search Report for PCT/KR2020/011814 dated Dec. 7, 2020 (PCT/ISA/210).

(Continued)

*Primary Examiner* — Aurora M Fontainhas
(74) *Attorney, Agent, or Firm* — Sughrue Mion, PLLC

(57) ABSTRACT

Disclosed are a composition and method for the diagnosis of diseases accompanied by impaired glucose tolerance, comprising a material for ITIH1 detection. The composition and method according to the present application enable a relatively sensitive response even to small changes in blood sugar according to various stimulants in a hyperglycemic situation as compared to glycated hemoglobin (HbA1c) which is an existing diagnostic marker widely used for patients with diabetes, which is a typical disease accompanied by impaired glucose tolerance, and thus can more precisely detect blood sugar changes under various stress situations.

14 Claims, 7 Drawing Sheets

Specification includes a Sequence Listing.

(51) Int. Cl.
*G01N 33/563* (2006.01)
*G16H 50/30* (2018.01)

(52) U.S. Cl.
CPC ......... *G16H 50/30* (2018.01); *C07K 2317/24* (2013.01); *C07K 2317/30* (2013.01); *C07K 2317/565* (2013.01); *G01N 2800/042* (2013.01)

(56) References Cited

FOREIGN PATENT DOCUMENTS

| KR | 10-2016-0072027 A | 6/2016 |
| KR | 10-2018-0107013 A | 10/2018 |
| KR | 10-2019-0040765 A | 4/2019 |
| KR | 10-2019-0044079 A | 4/2019 |

OTHER PUBLICATIONS

Written Opinion of the International Searching Authority for PCT/KR2020/011814 dated, Dec. 7, 2020 (PCT/ISA/237).
International Preliminary Report on Patentability for PCT/KR2020/011814 dated, Mar. 8, 2022 (PCT/ISA/373).
Tae Hyun Kim, "Regulation of energy utilization by G12 family signaling", Thesis publication, Seoul National University, pp. 18-21, 68, 2016 (8 pages total).

[FIG. 1]
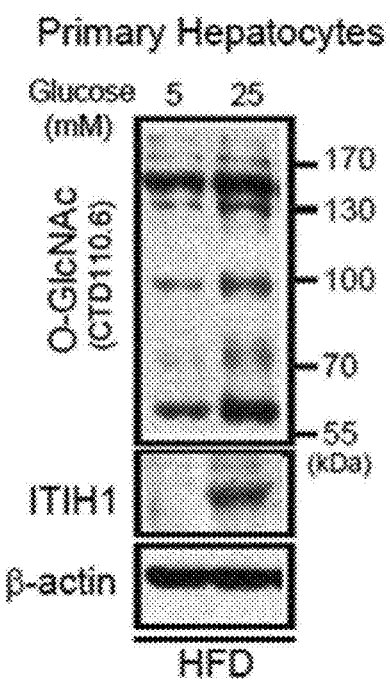
[FIG. 2]
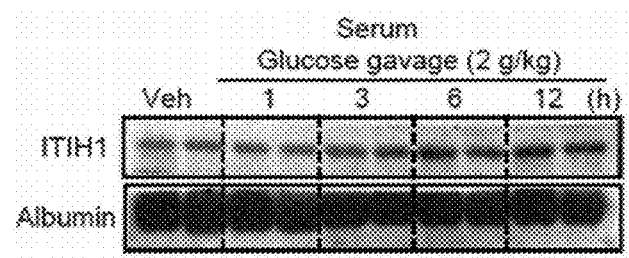

[FIG. 3A]
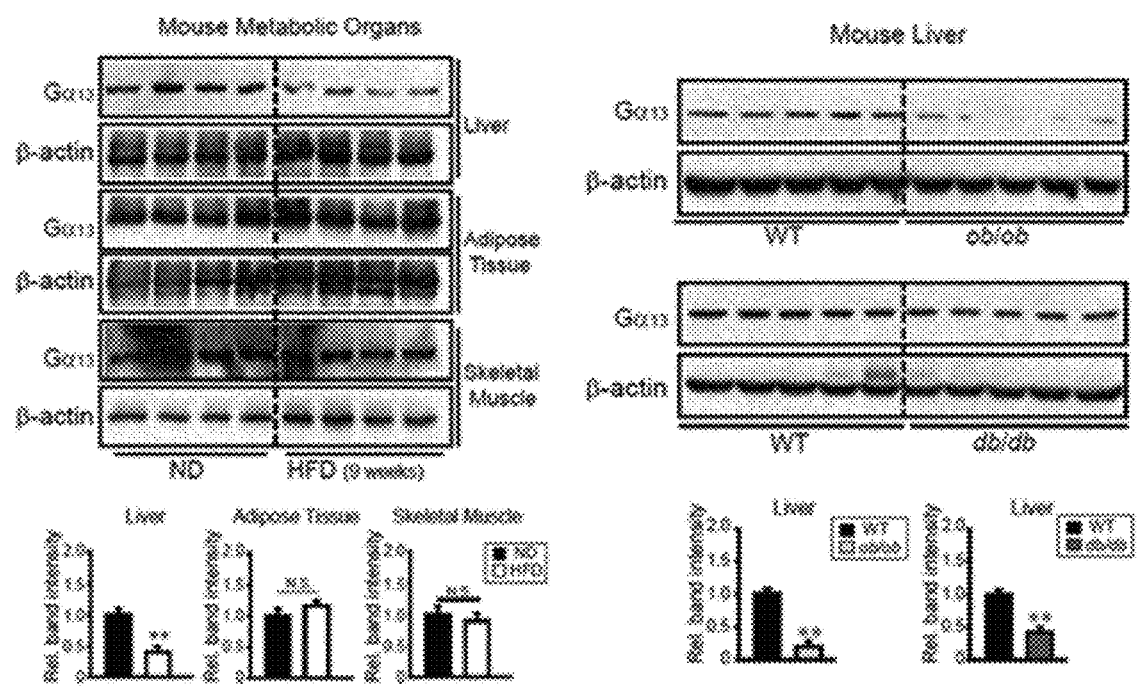
[FIG. 3B]
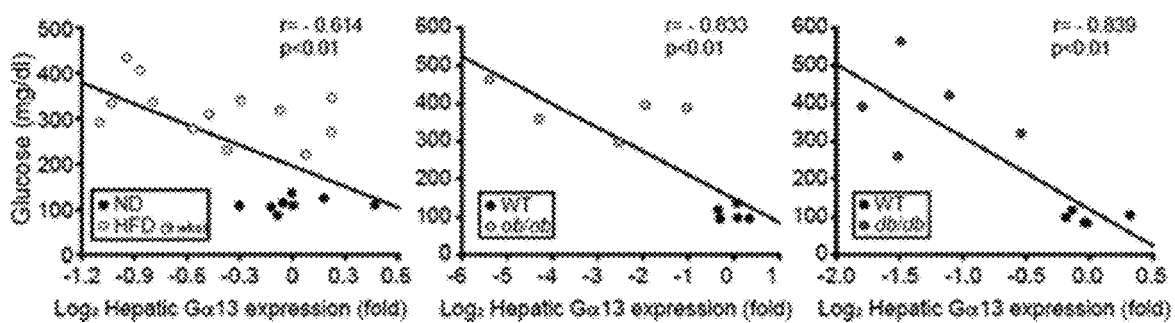

[FIG. 3C]
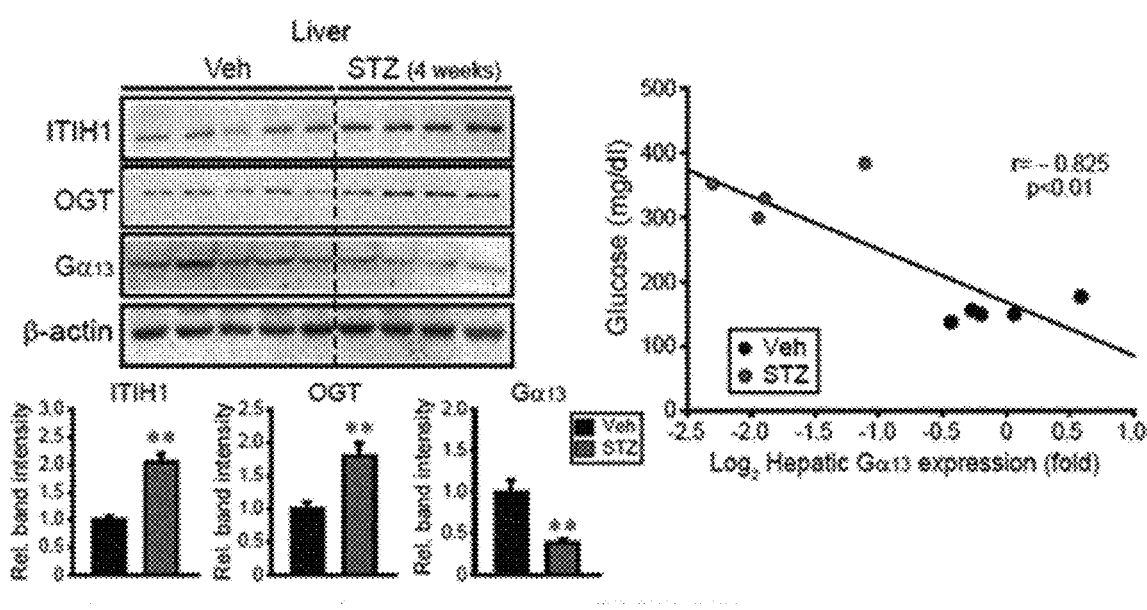

[FIG. 5]
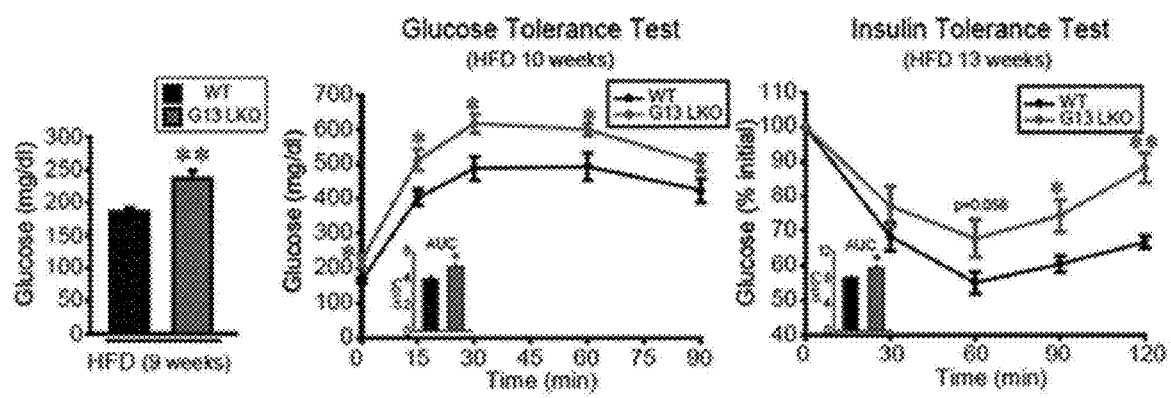
[FIG. 6]
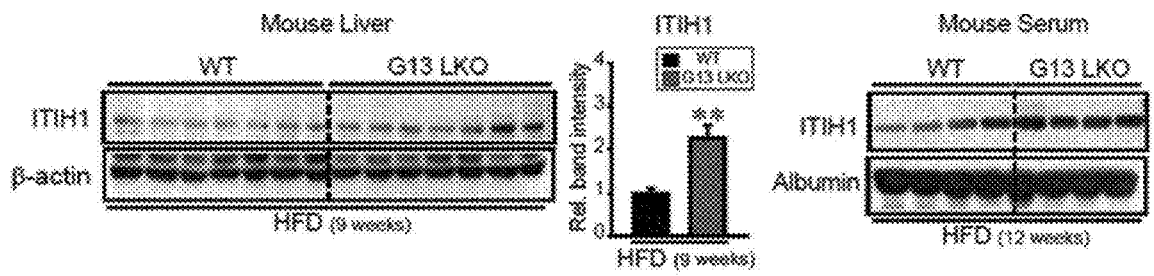

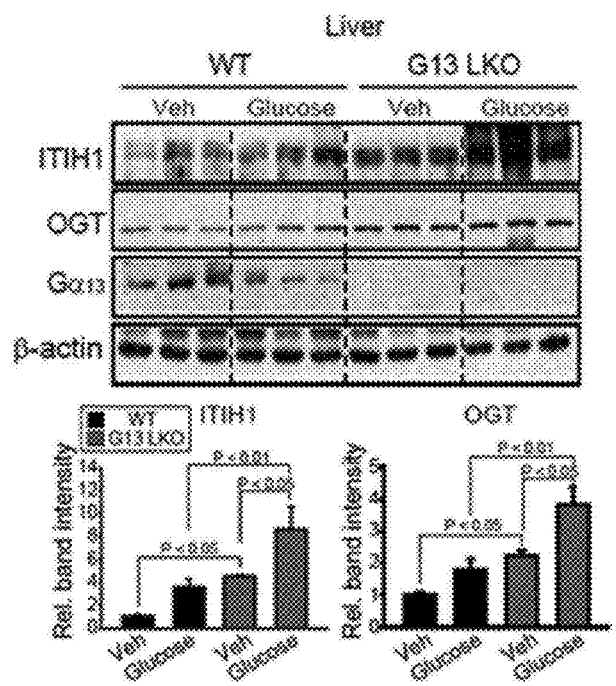
[FIG. 7]

```
SEQUENCE LISTING

<160> NUMBER OF SEQ ID NOS: 28

<210> SEQ ID NO 1
<211> LENGTH: 15
<212> TYPE: PRT
<213> ORGANISM: Artificial Sequence
<220> FEATURE:
<223> OTHER INFORMATION: 5D6 CDRL1

<400> SEQUENCE: 1

Arg Ala Ser Gln Ser Val Ser Thr Ser Ser Tyr Ser Tyr Met His
1               5                   10                  15

<210> SEQ ID NO 2
<211> LENGTH: 7
<212> TYPE: PRT
<213> ORGANISM: Artificial Sequence
<220> FEATURE:
<223> OTHER INFORMATION: 5D6 CDRL2

<400> SEQUENCE: 2

Tyr Ala Ser Asn Leu Glu Ser
1               5

<210> SEQ ID NO 3
<211> LENGTH: 9
<212> TYPE: PRT
<213> ORGANISM: Artificial Sequence
<220> FEATURE:
<223> OTHER INFORMATION: 5D6 CDRL3

<400> SEQUENCE: 3

Gln His Ser Trp Glu Ile Pro Trp Thr
1               5
```

```
<210> SEQ ID NO 4
<211> LENGTH: 5
<212> TYPE: PRT
<213> ORGANISM: Artificial Sequence
<220> FEATURE:
<223> OTHER INFORMATION: 5D6 CDRH1

<400> SEQUENCE: 4

Ser Tyr Trp Met His
1               5

<210> SEQ ID NO 5
<211> LENGTH: 17
<212> TYPE: PRT
<213> ORGANISM: Artificial Sequence
<220> FEATURE:
<223> OTHER INFORMATION: 5D6 CDRH2

<400> SEQUENCE: 5

Asp Ile Tyr Pro Gly Thr Asp Ser Thr Asn Tyr Asn Glu Lys Phe Lys
1               5                   10                  15

Ser

<210> SEQ ID NO 6
<211> LENGTH: 7
<212> TYPE: PRT
<213> ORGANISM: Artificial Sequence
<220> FEATURE:
<223> OTHER INFORMATION: 5D6 CDRH3

<400> SEQUENCE: 6

Ser Gly Asp Tyr Tyr Asp Tyr
1               5

<210> SEQ ID NO 7
<211> LENGTH: 15
<212> TYPE: PRT
<213> ORGANISM: Artificial Sequence
<220> FEATURE:
<223> OTHER INFORMATION: 9E1 CDRL1

<400> SEQUENCE: 7

Arg Ala Ser Gln Ser Val Ser Thr Ser Ser Tyr Ser Tyr Met His
1               5                   10                  15

<210> SEQ ID NO 8
<211> LENGTH: 7
<212> TYPE: PRT
<213> ORGANISM: Artificial Sequence
<220> FEATURE:
<223> OTHER INFORMATION: 9E1 CDRL2

<400> SEQUENCE: 8

Tyr Ala Ser Asn Leu Glu Ser
1               5

<210> SEQ ID NO 9
<211> LENGTH: 9
<212> TYPE: PRT
<213> ORGANISM: Artificial Sequence
<220> FEATURE:
<223> OTHER INFORMATION: 9E1 CDRL3

<400> SEQUENCE: 9

Gln His Ser Trp Glu Ile Pro Pro Thr
```

```
1               5

<210> SEQ ID NO 10
<211> LENGTH: 5
<212> TYPE: PRT
<213> ORGANISM: Artificial Sequence
<220> FEATURE:
<223> OTHER INFORMATION: 9E1 CDRH1

<400> SEQUENCE: 10

Ser Tyr Trp Met His
1               5

<210> SEQ ID NO 11
<211> LENGTH: 17
<212> TYPE: PRT
<213> ORGANISM: Artificial Sequence
<220> FEATURE:
<223> OTHER INFORMATION: 9E1 CDRH2

<400> SEQUENCE: 11

Ser Ile Tyr Pro Gly Asn Thr Asp Thr Asn Tyr Asn Gln Lys Phe Lys
1               5                   10                  15

Gly

<210> SEQ ID NO 12
<211> LENGTH: 9
<212> TYPE: PRT
<213> ORGANISM: Artificial Sequence
<220> FEATURE:
<223> OTHER INFORMATION: 9E1 CDRH3

<400> SEQUENCE: 12

Tyr Gly Thr Ser Glu Gly Phe Ala Tyr
1               5

<210> SEQ ID NO 13
<211> LENGTH: 111
<212> TYPE: PRT
<213> ORGANISM: Artificial Sequence
<220> FEATURE:
<223> OTHER INFORMATION: 5D6 Light chain variable region

<400> SEQUENCE: 13

Asp Ile Val Leu Thr Gln Ser Pro Ala Ser Leu Ala Val Ser Leu Gly
1               5                   10                  15

Gln Arg Ala Thr Ile Ser Cys Arg Ala Ser Gln Ser Val Ser Thr Ser
                20                  25                  30

Ser Tyr Ser Tyr Met His Trp Tyr Gln Gln Lys Pro Gly Gln Pro Pro
            35                  40                  45

Lys Leu Leu Ile Lys Tyr Ala Ser Asn Leu Glu Ser Gly Val Pro Ala
        50                  55                  60

Arg Phe Ser Gly Ser Gly Ser Gly Thr Asp Phe Thr Leu Asn Ile His
65                  70                  75                  80

Pro Val Glu Glu Glu Asp Thr Ala Thr Tyr Tyr Cys Gln His Ser Trp
                85                  90                  95

Glu Ile Pro Trp Thr Phe Gly Gly Gly Thr Lys Leu Glu Ile Lys
            100                 105                 110

<210> SEQ ID NO 14
<211> LENGTH: 116
<212> TYPE: PRT
<213> ORGANISM: Artificial Sequence
```

```
<220> FEATURE:
<223> OTHER INFORMATION: 5D6 Heavy chain variable region

<400> SEQUENCE: 14

Glu Val Gln Leu Gln Gln Ser Gly Ala Glu Leu Val Lys Pro Gly Thr
1               5                   10                  15

Ser Val Lys Met Ser Cys Lys Ala Ser Gly Tyr Thr Phe Thr Ser Tyr
            20                  25                  30

Trp Met His Trp Val Arg Gln Arg Pro Gly Gln Gly Leu Glu Trp Ile
        35                  40                  45

Gly Asp Ile Tyr Pro Gly Thr Asp Ser Thr Asn Tyr Asn Glu Lys Phe
    50                  55                  60

Lys Ser Lys Ala Thr Leu Thr Val Asp Thr Ser Ser Thr Ala Tyr
65                  70                  75                  80

Met Gln Leu Ser Ser Leu Thr Ser Glu Asp Ser Ala Val Tyr Tyr Cys
                85                  90                  95

Ser Arg Ser Gly Asp Tyr Tyr Asp Tyr Trp Gly Gln Gly Thr Thr Val
            100                 105                 110

Thr Val Ser Ser
        115

<210> SEQ ID NO 15
<211> LENGTH: 111
<212> TYPE: PRT
<213> ORGANISM: Artificial Sequence
<220> FEATURE:
<223> OTHER INFORMATION: 9E1 Light chain variable region

<400> SEQUENCE: 15

Asp Ile Val Met Thr Gln Ser Pro Ala Ser Leu Ala Val Ser Leu Gly
1               5                   10                  15

Gln Arg Ala Thr Ile Ser Cys Arg Ala Ser Gln Ser Val Ser Thr Ser
            20                  25                  30

Ser Tyr Ser Tyr Met His Trp Tyr Gln Gln Lys Pro Gly Gln Pro Pro
        35                  40                  45

Lys Leu Leu Ile Lys Tyr Ala Ser Asn Leu Glu Ser Gly Val Pro Ala
    50                  55                  60

Arg Phe Ser Gly Ser Gly Ser Gly Thr Asp Phe Thr Leu Asn Ile His
65                  70                  75                  80

Pro Val Glu Glu Glu Asp Ser Ala Thr Tyr Tyr Cys Gln His Ser Trp
                85                  90                  95

Glu Ile Pro Pro Thr Phe Gly Gly Gly Thr Lys Leu Glu Ile Lys
            100                 105                 110

<210> SEQ ID NO 16
<211> LENGTH: 118
<212> TYPE: PRT
<213> ORGANISM: Artificial Sequence
<220> FEATURE:
<223> OTHER INFORMATION: 9E1 Heavy chain variable region

<400> SEQUENCE: 16

Glu Val Gln Leu Gln Gln Ser Gly Thr Val Leu Ala Arg Pro Gly Ala
1               5                   10                  15

Ser Val Lys Met Ser Cys Arg Ala Ser Gly Tyr Ser Phe Thr Ser Tyr
            20                  25                  30

Trp Met His Trp Val Lys Gln Arg Pro Gly Gln Gly Leu Glu Trp Ile
        35                  40                  45
```

```
Gly Ser Ile Tyr Pro Gly Asn Thr Asp Thr Asn Tyr Asn Gln Lys Phe
    50                  55                  60

Lys Gly Lys Ala Lys Leu Thr Ala Val Thr Ser Ala Ser Thr Ala Tyr
65                  70                  75                  80

Met Glu Leu Ser Ser Leu Thr Asn Glu Asp Ser Ala Val Tyr Tyr Cys
                85                  90                  95

Thr Arg Tyr Gly Thr Ser Glu Gly Phe Ala Tyr Trp Gly Gln Gly Thr
            100                 105                 110

Leu Val Thr Val Ser Ala
        115
```

```
<210> SEQ ID NO 17
<211> LENGTH: 15
<212> TYPE: PRT
<213> ORGANISM: Artificial Sequence
<220> FEATURE:
<223> OTHER INFORMATION: 5D6 epitope

<400> SEQUENCE: 17

Glu Ala Leu Leu Lys Ile Leu Gly Asp Met Gln Pro Gly Asp Tyr
1               5                   10                  15
```

```
<210> SEQ ID NO 18
<211> LENGTH: 11
<212> TYPE: PRT
<213> ORGANISM: Artificial Sequence
<220> FEATURE:
<223> OTHER INFORMATION: 5D6 epitope

<400> SEQUENCE: 18

Glu Phe Ser Ile Thr Cys Leu Val Asp Glu Glu
1               5                   10
```

```
<210> SEQ ID NO 19
<211> LENGTH: 13
<212> TYPE: PRT
<213> ORGANISM: Artificial Sequence
<220> FEATURE:
<223> OTHER INFORMATION: 5D6 epitope

<400> SEQUENCE: 19

Ile Gly Phe Glu Val Ser Asp Ile His Pro Gly Ser Asp
1               5                   10
```

```
<210> SEQ ID NO 20
<211> LENGTH: 15
<212> TYPE: PRT
<213> ORGANISM: Artificial Sequence
<220> FEATURE:
<223> OTHER INFORMATION: 5D6 epitope

<400> SEQUENCE: 20

His Asn Asn Gly Ala Gly Leu Ile Asp Gly Ala Tyr Thr Asp Tyr
1               5                   10                  15
```

```
<210> SEQ ID NO 21
<211> LENGTH: 6
<212> TYPE: PRT
<213> ORGANISM: Artificial Sequence
<220> FEATURE:
<223> OTHER INFORMATION: 5D6 epitope

<400> SEQUENCE: 21

Ile Ala Val Glu Trp Glu
1               5
```

<210> SEQ ID NO 22
<211> LENGTH: 4
<212> TYPE: PRT
<213> ORGANISM: Artificial Sequence
<220> FEATURE:
<223> OTHER INFORMATION: 9E1 epitope

<400> SEQUENCE: 22

Ile Ser Asp Phe
1

<210> SEQ ID NO 23
<211> LENGTH: 12
<212> TYPE: PRT
<213> ORGANISM: Artificial Sequence
<220> FEATURE:
<223> OTHER INFORMATION: 9E1 epitope

<400> SEQUENCE: 23

Asn Thr Gln Arg Leu Pro Asp Arg Val Thr Gly Val
1               5                   10

<210> SEQ ID NO 24
<211> LENGTH: 1143
<212> TYPE: PRT
<213> ORGANISM: Homo sapiens
<220> FEATURE:
<221> NAME/KEY: PEPTIDE
<222> LOCATION: (1)..(27)
<223> OTHER INFORMATION: Human ITIH1 fused to Fc_ ITIH1 Signal peptide
<220> FEATURE:
<221> NAME/KEY: PEPTIDE
<222> LOCATION: (28)..(912)
<223> OTHER INFORMATION: Human ITIH1 fused to Fc_ ITIH1 (propeptide-
    chain-propeptide)
<220> FEATURE:
<221> NAME/KEY: PEPTIDE
<222> LOCATION: (913)..(1143)
<223> OTHER INFORMATION: Human ITIH1 fused to Fc_ Fc(Hinge, CH2, CH3 of
    Immunoglobulin gamma-1 heavy chain)

<400> SEQUENCE: 24

Met Asp Gly Ala Met Gly Pro Arg Gly Leu Leu Leu Cys Met Tyr Leu
1               5                   10                  15

Val Ser Leu Leu Ile Leu Gln Ala Met Pro Ala Leu Gly Ser Ala Thr
            20                  25                  30

Gly Arg Ser Lys Ser Ser Glu Lys Arg Gln Ala Val Asp Thr Ala Val
        35                  40                  45

Asp Gly Val Phe Ile Arg Ser Leu Lys Val Asn Cys Lys Val Thr Ser
    50                  55                  60

Arg Phe Ala His Tyr Val Val Thr Ser Gln Val Val Asn Thr Ala Asn
65                  70                  75                  80

Glu Ala Arg Glu Val Ala Phe Asp Leu Glu Ile Pro Lys Thr Ala Phe
                85                  90                  95

Ile Ser Asp Phe Ala Val Thr Ala Asp Gly Asn Ala Phe Ile Gly Asp
            100                 105                 110

Ile Lys Asp Lys Val Thr Ala Trp Lys Gln Tyr Arg Lys Ala Ala Ile
        115                 120                 125

Ser Gly Glu Asn Ala Gly Leu Val Arg Ala Ser Gly Arg Thr Met Glu
    130                 135                 140

Gln Phe Thr Ile His Leu Thr Val Asn Pro Gln Ser Lys Val Thr Phe
145                 150                 155                 160

```
Gln Leu Thr Tyr Glu Glu Val Leu Lys Arg Asn His Met Gln Tyr Glu
            165                 170                 175
Ile Val Ile Lys Val Lys Pro Lys Gln Leu Val His His Phe Glu Ile
        180                 185                 190
Asp Val Asp Ile Phe Glu Pro Gln Gly Ile Ser Lys Leu Asp Ala Gln
        195                 200                 205
Ala Ser Phe Leu Pro Lys Glu Leu Ala Ala Gln Thr Ile Lys Lys Ser
    210                 215                 220
Phe Ser Gly Lys Lys Gly His Val Leu Phe Arg Pro Thr Val Ser Gln
225                 230                 235                 240
Gln Gln Ser Cys Pro Thr Cys Ser Thr Ser Leu Leu Asn Gly His Phe
            245                 250                 255
Lys Val Thr Tyr Asp Val Ser Arg Asp Lys Ile Cys Asp Leu Leu Val
            260                 265                 270
Ala Asn Asn His Phe Ala His Phe Ala Pro Gln Asn Leu Thr Asn
            275                 280                 285
Met Asn Lys Asn Val Val Phe Val Ile Asp Ile Ser Gly Ser Met Arg
            290                 295                 300
Gly Gln Lys Val Lys Gln Thr Lys Glu Ala Leu Leu Lys Ile Leu Gly
305                 310                 315                 320
Asp Met Gln Pro Gly Asp Tyr Phe Asp Leu Val Leu Phe Gly Thr Arg
                325                 330                 335
Val Gln Ser Trp Lys Gly Ser Leu Val Gln Ala Ser Glu Ala Asn Leu
            340                 345                 350
Gln Ala Ala Gln Asp Phe Val Arg Gly Phe Ser Leu Asp Glu Ala Thr
        355                 360                 365
Asn Leu Asn Gly Gly Leu Leu Arg Gly Ile Glu Ile Leu Asn Gln Val
    370                 375                 380
Gln Glu Ser Leu Pro Glu Leu Ser Asn His Ala Ser Ile Leu Ile Met
385                 390                 395                 400
Leu Thr Asp Gly Asp Pro Thr Glu Gly Val Thr Asp Arg Ser Gln Ile
                405                 410                 415
Leu Lys Asn Val Arg Asn Ala Ile Arg Gly Arg Phe Pro Leu Tyr Asn
            420                 425                 430
Leu Gly Phe Gly His Asn Val Asp Phe Asn Phe Leu Glu Val Met Ser
        435                 440                 445
Met Glu Asn Asn Gly Arg Ala Gln Arg Ile Tyr Glu Asp His Asp Ala
    450                 455                 460
Thr Gln Gln Leu Gln Gly Phe Tyr Ser Gln Val Ala Lys Pro Leu Leu
465                 470                 475                 480
Val Asp Val Asp Leu Gln Tyr Pro Gln Asp Ala Val Leu Ala Leu Thr
                485                 490                 495
Gln Asn His His Lys Gln Tyr Tyr Glu Gly Ser Glu Ile Val Val Ala
            500                 505                 510
Gly Arg Ile Ala Asp Asn Lys Gln Ser Ser Phe Lys Ala Asp Val Gln
        515                 520                 525
Ala His Gly Glu Gly Gln Glu Phe Ser Ile Thr Cys Leu Val Asp Glu
    530                 535                 540
Glu Glu Met Lys Lys Leu Leu Arg Glu Arg Gly His Met Leu Glu Asn
545                 550                 555                 560
His Val Glu Arg Leu Trp Ala Tyr Leu Thr Ile Gln Glu Leu Leu Ala
                565                 570                 575
Lys Arg Met Lys Val Asp Arg Glu Glu Arg Ala Asn Leu Ser Ser Gln
```

```
                580             585             590
Ala Leu Gln Met Ser Leu Asp Tyr Gly Phe Val Thr Pro Leu Thr Ser
            595                 600             605

Met Ser Ile Arg Gly Met Ala Asp Gln Asp Gly Leu Lys Pro Thr Ile
            610                 615             620

Asp Lys Pro Ser Glu Asp Ser Pro Pro Leu Glu Met Leu Gly Pro Arg
625                 630                 635                 640

Arg Thr Phe Val Leu Ser Ala Leu Gln Pro Ser Pro Thr His Ser Ser
                645                 650                 655

Ser Asn Thr Gln Arg Leu Pro Asp Arg Val Thr Gly Val Asp Thr Asp
            660                 665             670

Pro His Phe Ile Ile His Val Pro Gln Lys Glu Asp Thr Leu Cys Phe
            675                 680             685

Asn Ile Asn Glu Glu Pro Gly Val Ile Leu Ser Leu Val Gln Asp Pro
            690                 695             700

Asn Thr Gly Phe Ser Val Asn Gly Gln Leu Ile Gly Asn Lys Ala Arg
705                 710                 715                 720

Ser Pro Gly Gln His Asp Gly Thr Tyr Phe Gly Arg Leu Gly Ile Ala
                725                 730                 735

Asn Pro Ala Thr Asp Phe Gln Leu Glu Val Thr Pro Gln Asn Ile Thr
            740                 745             750

Leu Asn Pro Gly Phe Gly Gly Pro Val Phe Ser Trp Arg Asp Gln Ala
            755                 760             765

Val Leu Arg Gln Asp Gly Val Val Thr Ile Asn Lys Lys Arg Asn
            770                 775             780

Leu Val Val Ser Val Asp Asp Gly Gly Thr Phe Glu Val Val Leu His
785                 790                 795                 800

Arg Val Trp Lys Gly Ser Ser Val His Gln Asp Phe Leu Gly Phe Tyr
                805                 810                 815

Val Leu Asp Ser His Arg Met Ser Ala Arg Thr His Gly Leu Leu Gly
            820                 825             830

Gln Phe Phe His Pro Ile Gly Phe Glu Val Ser Asp Ile His Pro Gly
            835                 840             845

Ser Asp Pro Thr Lys Pro Asp Ala Thr Met Val Val Arg Asn Arg Arg
850                 855                 860

Leu Thr Val Thr Arg Gly Leu Gln Lys Asp Tyr Ser Lys Asp Pro Trp
865                 870                 875                 880

His Gly Ala Glu Val Ser Cys Trp Phe Ile His Asn Asn Gly Ala Gly
                885                 890                 895

Leu Ile Asp Gly Ala Tyr Thr Asp Tyr Ile Val Pro Asp Ile Phe Glu
            900                 905             910

Pro Lys Ser Ser Asp Lys Thr His Thr Ser Pro Pro Cys Pro Ala Pro
            915                 920             925

Glu Leu Leu Gly Gly Pro Ser Val Phe Leu Phe Pro Pro Lys Pro Lys
            930                 935             940

Asp Thr Leu Met Ile Ser Arg Thr Pro Glu Val Thr Cys Val Val Val
945                 950                 955                 960

Asp Val Ser His Glu Asp Pro Glu Val Lys Phe Asn Trp Tyr Val Asp
                965                 970                 975

Gly Val Glu Val His Asn Ala Lys Thr Lys Pro Arg Glu Glu Gln Tyr
            980                 985             990

Asn Ser Thr Tyr Arg Val Val Ser Val Leu Thr Val Leu His Gln Asp
            995                 1000            1005
```

Trp Leu Asn Gly Lys Glu Tyr Lys Cys Lys Val Ser Asn Lys Ala Leu
          1010                1015                1020

Pro Ala Pro Ile Glu Lys Thr Ile Ser Lys Ala Lys Gly Gln Pro Arg
1025                1030                1035                1040

Glu Pro Gln Val Tyr Thr Leu Pro Pro Ser Arg Asp Glu Leu Thr Lys
              1045                1050                1055

Asn Gln Val Ser Leu Thr Cys Leu Val Lys Gly Phe Tyr Pro Ser Asp
              1060                1065                1070

Ile Ala Val Glu Trp Glu Ser Asn Gly Gln Pro Glu Asn Asn Tyr Lys
          1075                1080                1085

Thr Thr Pro Pro Val Leu Asp Ser Asp Gly Ser Phe Phe Leu Tyr Ser
          1090                1095                1100

Lys Leu Thr Val Asp Lys Ser Arg Trp Gln Gln Gly Asn Val Phe Ser
1105                1110                1115                1120

Cys Ser Val Met His Glu Ala Leu His Asn His Tyr Thr Gln Lys Ser
              1125                1130                1135

Leu Ser Leu Ser Pro Gly Lys
          1140

<210> SEQ ID NO 25
<211> LENGTH: 333
<212> TYPE: DNA
<213> ORGANISM: Artificial Sequence
<220> FEATURE:
<223> OTHER INFORMATION: Nucleic acid encoding 5D6 LC Variable Region

<400> SEQUENCE: 25
gatattgtgc tgacccaatc tcctgcttcc ttagctgtat ctctggggca gagggccacc      60
atctcatgca gggccagcca aagtgtcagt acatctagct atagttatat gcactggtac     120
caacagaaac caggacagcc acccaaactc ctcatcaagt atgcatccaa cctagaatct     180
ggggtccctg ccaggttcag tggcagtggg tctgggacag acttcaccct caacatccat     240
cctgtggagg aggaggatac tgcaacatat tactgtcagc acagttggga gattccgtgg     300
acgttcggtg agggaccaa actggaaatc aaa                                   333

<210> SEQ ID NO 26
<211> LENGTH: 348
<212> TYPE: DNA
<213> ORGANISM: Artificial Sequence
<220> FEATURE:
<223> OTHER INFORMATION: Nucleic acid encoding 5D6 HC Variable Region

<400> SEQUENCE: 26
gaggtccagc tgcaacagtc tggggctgaa ctggtgaagc ctgggacttc agtgaaaatg      60
tcctgcaagg cttctggcta caccttcacc agctactgga tgcactgggt gaggcagagg     120 ccggacaag gccttgagtg gattggagat atttatcctg gtactgatag tactaactac     180
aatgagaagt tcaagagcaa ggccacactg actgtagaca catcctccag cacagcctac     240
atgcaactca gcagcctgac atctgaggac tctgcggtct attactgttc aagatcggga     300
gattactacg actactgggg ccaaggcacc acggtcaccg tctcctca                  348

<210> SEQ ID NO 27
<211> LENGTH: 333
<212> TYPE: DNA
<213> ORGANISM: Artificial Sequence
<220> FEATURE:
<223> OTHER INFORMATION: Nucleic acid encoding 9E1 LC Variable Region -continued

```
<400> SEQUENCE: 27
gatattgtga tgacccagtc tcctgcttcc ttagctgtat ctctggggca gagggccacc      60
atctcatgca gggccagcca aagtgtcagt acatctagct atagttatat gcactggtac     120
caacagaaac caggacagcc acccaaactc ctcatcaagt atgcatccaa cctagaatct     180
ggggtccctg ccaggttcag tggcagtggg tctgggacag acttcaccct caacatccat     240
cctgtggagg aggaggattc tgcaacatat tactgtcagc acagttggga gattcctccg     300
acgttcggtg gagggaccaa actggaaatc aaa                                  333

<210> SEQ ID NO 28
<211> LENGTH: 354
<212> TYPE: DNA
<213> ORGANISM: Artificial Sequence
<220> FEATURE:
<223> OTHER INFORMATION: Nucleic acid encoding 9E1 HC Variable Region

<400> SEQUENCE: 28
gaggttcagc tgcagcagtc tgggactgtg ctggcaaggc ctggggcttc cgtgaagatg      60
tcctgcaggg cttctggcta cagctttacc agctactgga tgcactgggt aaaacagagg     120
cctggacagg gtctagaatg gattggttct atttatcctg gaaatactga tactaactac     180
aaccagaagt tcaagggcaa ggccaaactg actgcagtca catccgccag cactgcctac     240
atggagctca gcagcctgac aaatgaggac tctgcggtct attactgtac aagatatggt     300
acttccgagg ggtttgctta ctggggccaa gggactctgg tcactgtctc tgca            354
```

USE OF ITIH1 AS BIOMARKER FOR DETECTION OF INSULIN RESISTANCE IN DISEASES ACCOMPANIED BY IMPAIRED GLUCOSE TOLERANCE

CROSS REFERENCE TO RELATED APPLICATIONS

This application is a National Stage of International Application No. PCT/KR2020/011814 filed Sep. 3, 2020, claiming priority based on Korean Patent Application No. 10-2019-0109433 filed Sep. 4, 2019.

SEQUENCE LISTING

The content of the electronically submitted sequence listing, file name: Sequence_Listing_As_Filed.txt; size: 20,266 bytes; and date of creation: May 3, 2022, filed herewith, is incorporated herein by reference in its entirety.

TECHNICAL FIELD

The present invention relates to the use of ITIH1 for the detection of insulin resistance in diseases accompanied by impaired glucose tolerance.

BACKGROUND ART

Hyperglycemia accompanied by impaired glucose tolerance is often caused by various types of stressors, toxic stimuli and inflammation that affect cells or tissues, or accompanies the progression of systemic metabolic syndromes including obesity or diabetes. Hyperglycemia is induced by pathological conditions such as excessive glucose production in the liver and decreased glucose utilization in peripheral tissues.

To date, it has been difficult to specify a sophisticated and highly reproducible biomarker indicative of the severity of hyperglycemia, so methods for searching for substances having an effect of ameliorating hyperglycemia in a specific target have not been successful.

Korean Patent Laid-open Publication No. 2016-0072027 discloses the use of ITIH1 as a biomarker for diagnosing liver cancer.

Korean Patent Laid-open Publication No. 2013-0079951 discloses a marker for early diagnosis of diabetic retinopathy, which is a complication of diabetes.

Therefore, there is a need for the development of a novel biomarker enabling early analysis of hyperglycemia caused by metabolic syndromes using a small amount of patient blood obtained in a non-invasive manner.

DISCLOSURE

Technical Problem

It is an object of the present invention to provide a biomarker enabling early analysis of hyperglycemia caused by a variety of metabolic syndromes using a small amount of patient blood obtained in a non-invasive manner.

Technical Solution

In accordance with one aspect of the present invention, the above and other objects can be accomplished by the provision of a composition for detecting insulin resistance in subjects having diseases accompanied by impaired glucose tolerance or diseases accompanied by hyperglycemia, the composition containing a substance for detecting an inter-alpha trypsin inhibitor heavy chain 1 (ITIH1).

Regarding the diseases accompanied by impaired glucose tolerance or the diseases accompanied by hyperglycemia, or the diseases causing the symptom include, but are not limited to, metabolic syndromes, type 1 diabetes mellitus, type 2 diabetes mellitus, diabetic nephropathy, inflammatory bowel diseases including Crohn's disease or ulcerative colitis, obesity, hyperlipidemia, fat hepatitis, steatohepatitis, liver fibrosis or cirrhosis, kidney disease, muscle disease, and dementia.

The marker according to the present invention may be detected at the level of proteins or nucleic acids, and thus the composition may contain a reagent required therefor. For example, detection of the marker at the protein level according to the present invention may be performed by western blot, ELISA, radioimmunoassay, immunodiffusion, immunoelectrophoresis, tissue immunostaining, immunoprecipitation assay, complement fixation assay, FACS, mass spectrometry, or protein microarray, and the reagent for detection may specifically be an antibody that recognizes the full-length protein of the marker or a fragment thereof, an antibody fragment, an aptamer, an avidity multimer or a peptidomimetic. The marker may be detected at the level of nucleic acids, for example, mRNA. For example, the detection may be performed by polymerase chain reaction, reverse transcription polymerase chain reaction, competitive polymerase chain reaction, nuclease protection assay (RNase, S1 nuclease assay), in-situ hybridization, nucleic acid microarray, or northern blot, and such a reagent for detection includes a nucleic acid sequence of the marker, a nucleic acid sequence complementary to the nucleic acid sequence, and a primer pair and/or probe that specifically recognizes a fragment of the nucleic acid sequence and the sequence complementary thereto.

The present invention provides an antibody or antigen-binding fragment that specifically recognizes an inter-alpha trypsin inhibitor heavy chain 1 (ITIH1).

In one embodiment, the marker according to the present invention is detected using an antibody, wherein the antibody includes a light-chain variable region including the complementarity-determining regions CDRL1, CDRL2, and CDRL3 set forth in SEQ ID NOS: 1, 2, and 3, respectively, and a heavy-chain variable region including the complementarity-determining regions CDRH1, CDRH2, and CDRH3 set forth in SEQ ID NOS: 4, 5, and 6, respectively, or a light-chain variable region including the complementarity-determining regions CDRL1, CDRL2, and CDRL3 set forth in SEQ ID NOS: 7, 8, and 9, respectively, and a heavy-chain variable region including the complementarity-determining regions CDRH1, CDRH2, and CDRH3 set forth in SEQ ID NOS: 10, 11, and 12, respectively.

In another aspect, the present invention provides a kit for diagnosing diseases accompanied by impaired glucose tolerance, including a detection reagent for an inter-alpha trypsin inhibitor heavy chain 1 (ITIH1) marker and further including instructions for use and the like.

In another aspect, the present invention provides a method for detecting an ITIH1 biomarker in vitro in order to provide information necessary for the diagnosis or prognosis of a disease accompanied by impaired glucose tolerance, the method including detecting the presence and/or concentration of the nucleic acid and/or protein of the ITIH1 biomarker from a biological sample derived from a test subject, comparing the result of detection for the concentration or presence of the nucleic acid, particularly mRNA, or protein with the result of the corresponding marker in a normal control sample, and determining that there is a disease accompanied by impaired glucose tolerance when, compared to the normal control sample, there is a change in the concentration of nucleic acid or protein in the sample derived from the subject, or there is a change with regard to the presence or absence of the nucleic acid or protein, particularly when the content of the nucleic acid or protein increases.

The biological sample or specimen used in the method according to the present invention includes serum, or liver cells or liver tissue containing primary hepatocytes and established hepatocytes.

In one embodiment, the method according to the present invention is performed by a method, for example, ELISA or Western blot, of detecting a protein using an antibody that specifically recognizes ITIH1.

In one embodiment, the antibody used in the method includes a light-chain variable region including the complementarity-determining regions CDRL1, CDRL2, and CDRL3 set forth in SEQ ID NOS: 1, 2, and 3, respectively, and a heavy-chain variable region including the complementarity-determining regions CDRH1, CDRH2, and CDRH3 set forth in SEQ ID NOS: 4, 5, and 6, respectively, or a light-chain variable region including the complementarity-determining regions CDRL1, CDRL2, and CDRL3 set forth in SEQ ID NOS: 7, 8, and 9, respectively, and a heavy-chain variable region including the complementarity-determining regions CDRH1, CDRH2, and CDRH3 set forth in SEQ ID NOS: 10, 11, and 12, respectively.

In one embodiment, the comparing in the method according to the present invention may be performed using non-marker clinical information including HbA1c (glycated hemoglobin), postprandial blood glucose, fasting blood glucose, blood insulin concentration, HOMA-IR, C-peptide concentration, adipose tissue IR, various lipid indicators (total cholesterol, triglyceride, free fatty acid), BMI (body mass index), and NAFLD activity scores (NAS score; steatosis grade, lobular inflammation, and ballooning).

Advantageous Effects

ITIH1, which is changed by glucose stimulation according to the present invention, is useful as a biomarker for detecting a disease accompanied by impaired glucose tolerance or insulin resistance. In the case of conventional glycated hemoglobin (HbA1c), which is widely used as a diagnostic indicator for patients having diabetes, which is a typical disease accompanied by impaired glucose tolerance, the average value of blood glucose over the preceding 2-3 months is evaluated based on the time of diagnosis, and the measured value range of the indicator according to the severity of the disease is very narrow and reflects levels of accumulated chronically (or for a long period of time) due to the characteristics of glycated hemoglobin. Using only this indicator is limitedly effective in quickly and sensitively detecting changes in blood sugar due to diet, the presence or absence of stress, or diversification of symptoms. In contrast, ITIH1, which is a biomarker disclosed herein, responds relatively sensitively to small changes in insulin resistance and blood sugar caused by various stimuli in a hyperglycemic situation, so it can more precisely indicate changes in blood sugar under various stressful conditions.

DESCRIPTION OF DRAWINGS

FIG. 1 shows the result of analysis of variation in the level of O-GlcNAc of ITIH1 in the collected hepatocytes using antibodies of CTD110.6 clones, after primary hepatocytes isolated from the liver of liver-selective Ga13-knockout mice fed a high-lipid diet for 5 weeks were cultured, while 25 mM glucose stimulation was applied to the culture medium for 24 hours, wherein, compared with the low-concentration condition, O-GlcNAc of ITIH1 was increased by stimulation with a high concentration of glucose and the expression of ITIH1 was remarkably increased, and these results indicate that a cell-based assay that mimics the hyperglycemic situation in vivo was successfully established.

FIG. 2 shows the result of western blot analysis of serum ITIH1 expression levels at predetermined times in each of mice (two per group) to which a high concentration of glucose (2 g/kg body weight) was administered. Albumin was used in the same amount as the serum sample and was thus used for comparative evaluation. ITIH1 antibody (Biorbyt, Ltd., UK) and albumin antibody (Cusabio Technology LLC., USA) used as primary antibodies in the western blot experiment were analyzed using commercially available antibodies according to the manufacturer's experimental method. When glucose stimulation was applied, it was found that the content of ITIH1 was increased in the liver tissue and blood of mice, and ITIH1 expression was high in Ga13 gene-deficient mice even in the absence of glucose stimulation compared to normal mice. When glucose stimulation was applied to such mice, the ITIH1 content was very high. This is an effective method that is greatly improved compared to a conventional administration model fed a high-lipid diet for 12 to 16 weeks. The single glucose administration method proposed in the present invention is an experimental method capable of performing target analysis in the corresponding disease situation by easily establishing a hyperglycemia model even through a short-period simple experimental method and thus has advantages of overcoming consumption of a lot of time and money to actually induce hyperglycemia, while consuming a high-fat diet for about 12 to 16 weeks.

FIGS. 3A to 3C show the correlation between the change in the expression of liver Ga13 and blood sugar in various hyperglycemic animal models induced using high-lipid diet, a genetic modification that eliminates an appetite suppression center, and administration of streptozotocin (STZ). As a result, the expression of Ga13 in the liver was decreased in all tested hyperglycemia conditions, indicating that the change in Ga13 expression was directly correlated with hyperglycemia. In addition, the results indicate that the decrease in Ga13 expression and the increase in ITIH1 occur together.

FIGS. 4A and 4B show the results of detection of AAVLGESAGLVR and LDAQASFLSEELAAQTIK peptides of mouse ITIH1, respectively.

FIG. 5 shows the results of glucose tolerance and insulin tolerance tests performed on hepatocyte-selective Ga13-deficient mice fed a high-lipid diet for 9 to 13 weeks, and shows the state in which fasting blood glucose is significantly increased in the selective Ga13-deficient mice (left), the result of the glucose tolerance test (middle), and the result of the insulin tolerance test (right).

FIG. 6 shows the result of western blot analysis identifying the expression of ITIH1 in liver tissue and sera derived from normal mice or hepatocyte-selective Ga13-deficient mice fed a high-lipid diet, wherein an ITIH1 antibody (Biorbyt, UK), a beta-actin antibody (Sigma, USA) and an albumin antibody (Cusabio, USA) used as primary antibodies in the Western blot experiment were analyzed as commercially available antibodies in accordance with the experimental method suggested by the manufacturer, and FIG. 6 indicates that the expression of ITIH1 was remarkably increased in the livers and sera of Ga13-deficient mice compared to normal mice.

FIG. 7 shows the result of Western blot to determine the amount of ITIH1 in a sample obtained 6 hours after one-time oral administration of a high concentration of glucose (2 g/kg body weight) to normal mice or hepatocyte-selective Ga13-deficient mice, wherein an ITIH1 antibody (Biorbyt, UK), an OGT antibody (Sigma, USA), a Ga13 antibody (Santa Cruz, USA), and a beta-actin antibody (Sigma, USA), used as primary antibodies in the Western blot experiment, were analyzed as commercially available antibodies according to the manufacturer's experimental method, and FIG. 7 shows that the expression of ITIH1 and OGT increased along with the decrease of Ga13 when a high concentration of glucose was administered to normal mice, and the expression was further significantly increased in the livers of Ga13-deficient mice.

MODE FOR INVENTION

Figure 4A:
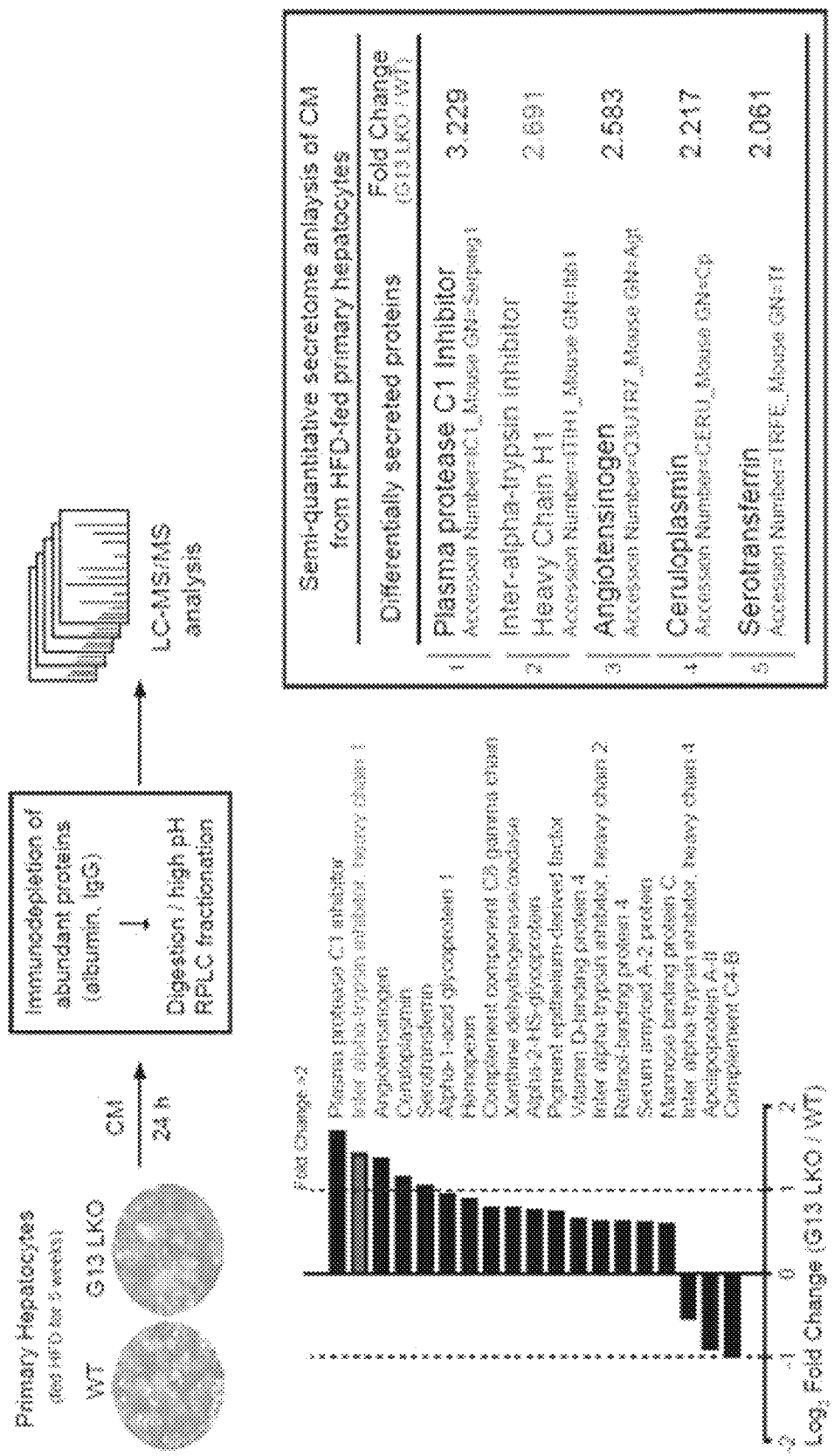
FIGS. 4A and 4B show a method for identifying a novel protein that is secreted from the Ga13-deficient liver and induces glucose intolerance using LC-MS, and results thereof.

The present invention is based on the finding of increase in liver tissue and blood concentration of ITIH1 (inter-alpha trypsin inhibitor heavy chain 1) by glucose stimulation and the mechanism thereof. Specifically, the present invention is based on the finding that an increase in OGT (O-GlcNAc transferase) attributable to a decrease in Ga13 (G protein alpha-13) in hyperglycemia increases the stability of ITIH1, thus causing an increase in intracellular concentration and secretion thereof. Accordingly, ITIH1, the expression of which is changed in response to glucose stimulation, as identified herein, is useful as a biomarker for detecting insulin resistance or impaired glucose tolerance in diseases accompanied by impaired glucose tolerance.

In the case of conventional glycated hemoglobin (HbA1c), which is widely used as a diagnostic indicator for patients having diabetes, which is a typical disease accompanied by impaired glucose tolerance, the average of blood glucose over the preceding 2-3 months is evaluated based on the time of diagnosis, and the measured value range of the indicator according to the severity of the disease is very narrow and reflects levels of accumulated chronically (or, for a long period of time) due to the characteristics of glycated hemoglobin. Therefore, using only this indicator entails limitations with regard to quickly and sensitively detecting changes in blood sugar due to diet, the presence or absence of stress, or diversification of symptoms. In contrast, ITIH1, which is a biomarker disclosed herein, responds relatively sensitively to small changes in blood sugar according to various stimuli in a hyperglycemic state, so it can more precisely indicate changes in blood sugar under various stressful conditions.

In one aspect, the present invention is directed to a composition for detecting a disease accompanied by impaired glucose tolerance containing a substance for detecting an inter-alpha trypsin inhibitor heavy chain 1 (ITIH1).

The disease accompanied by impaired glucose tolerance, the disease accompanied by insulin tolerance, or the disease accompanied by hyperglycemia includes, but is not limited to, metabolic syndromes, type 1 diabetes mellitus, type 2 diabetes mellitus, diabetic nephropathy, inflammatory bowel diseases including Crohn's disease or ulcerative colitis, obesity, hyperlipidemia, fat hepatitis, steatohepatitis, liver fibrosis or cirrhosis, kidney disease, muscle disease, and dementia.

As used herein, the term "metabolic disease" or "metabolic syndrome" refers to a group of diseases including risk factors of various cardiovascular diseases and type 2 diabetes. This is a helpful concept that can encompass and explain insulin resistance and related complicated and various metabolic abnormalities and clinical features. The metabolic syndrome increases the risk of cardiovascular disease or type 2 diabetes. It has been reported that the number of patients with metabolic syndrome increases explosively with the increase in the obese population. Insulin resistance caused by excessive weight and/or obesity is a key determinant of the chronic morbidity of energy metabolism abnormalities (diabetes), and induces chronic inflammatory conditions and cardiovascular abnormalities. Therefore, metabolic abnormalities promote the onset of cardiovascular diseases and are a fundamental cause of chronic intractable diseases that increase the risk of fatty accumulation and severe liver diseases in liver tissue (Anstee et al., Gastroenterology & Hepatology, 2013, Vol 10:330-344).

Hyperglycemia is classified as prediabetes when the fasting blood glucose level is 5.6 mM to 7 mM (100-126 mg/dl) in the human body, and diabetes when the fasting blood glucose level is 7 mM (126 mg/dl) or higher. When fasting blood glucose is randomly measured, if it exceeds 11.1 mM (200 mg/dl), it is classified as diabetes. However, pathological symptoms due to hyperglycemia are recognizable when the fasting blood glucose level reaches 15 mM to 20 mM (250-300 mg/dl). As used herein, the term "high-concentration glucose" means a concentration sufficient to cause an increase in concentration due to the mechanism identified herein, that is, activation of OGT attributable to reduction of Ga13 and stabilization of ITIH1 protein thereby. For example, the high-concentration glucose is from about 15 mM to about 35 mM, in particular about 25 mM. A normal concentration of glucose corresponds to about 3.9 mM to 7.1 mM (70-130 mg/dl), which is a fasting blood sugar level in humans, but an average fasting blood sugar in normal subjects is about 5.5 mM (100 mg/dl). As used herein, the term "insulin resistance" or "impaired glucose tolerance" includes blood sugar or hyperglycemia classified as prediabetes or diabetes as described above.

Here, ITIH1, the expression of which is increased in the presence of hyperglycemia, is one of the heavy chains constituting the inter-alpha-trypsin inhibitor complex (IaI), is called "serum-derived hyaluronan-associated protein (SHAP)" and is a protein produced in the liver cells and secreted into the blood. High expression of SHAP is observed at the site of the inflammatory reaction in the body of patients with rheumatoid arthritis or irritable bowel syndrome (inflammatory bowel disease). However, the expression regulation, mechanism and role of ITIH1 in hyperglycemia or systemic inflammatory and stressful situations other than local inflammatory environments have not been elucidated to date. In the case of a disease or physiological condition, regulation in the blood glucose concentration in the body varies. In particular, in metabolic syndromes accompanied by various stresses or insulin resistance, an excessive increase in blood sugar occurs, and if this situation continues, pathological reactions in the liver and various organs occur, causing tissue damage and dysfunction. Stimulation with a high concentration of glucose is directly related to insulin resistance and glucose toxicity, which can promote O-GlcNAc modification (O-GlcNAcylation) using glucose as a substrate. O-GlcNAcylation is mediated by an OGT enzyme and enables binding to serine/threonine residues of the target protein to induce GlcNAcylation modification, resulting in changes in the amount and function of the target.

The ITIH1 used herein may be obtained in a variety of forms depending on the specific analysis method, and examples thereof include those derived from mammals, particularly humans or mice. In addition, even when derived from the same type of host, for example, a human, there may be sequence variations depending on the specific individual, region, environment, etc. All variations, including sequences that have been modified (deleted, substituted, or added) but are functionally equivalent, may be used in the present invention.

The protein and gene sequences of ITIH1 used herein are known. For example, it is known that the NCBI (National Center for Biotechnology Information) gene and protein accession numbers for humans are NM_002215.4 and NP_002206.2, and the NCBI gene and protein accession numbers for mice are NM_008406.3 and NP_032432.2. However, the protein and gene sequences of ITIH1 are not limited to the above sequences, and include functional equivalents thereto.

As used herein, the term "diagnosis" refers to an action of determining whether or not a test subject has the susceptibility to a specific disease or disorder, determining whether or not a subject currently has a specific disease or disorder, determining the prognosis of a subject suffering from a specific disease or disorder (e.g., determining the stage or progression state of a disease, or determining the responsiveness of a disease to treatment), or performing therametrics (e.g., monitoring the condition of a subject in order to provide information about the therapeutic efficacy).

As used herein, the term "biomarker for diagnosis", "marker", or "diagnostic marker" refers to a substance that enables diagnosis on a sample, such as a cell or tissue, derived from a subject having a disease, differently from normal cells, or tissue or cells of a subject that has received appropriate treatment for a disease, and refers to a protein or nucleic acid that decreases in a sample derived from a subject having a disease compared to a normal sample.

As used herein, the term "biological sample" refers to a substance containing one or more components capable of detecting a biomarker, or a mixture of the substance, and includes cells, tissues, or body fluids derived from an organism, particularly a human, and examples thereof include, but are not limited to, whole blood, urine, plasma, and serum. The biological sample also includes cells or tissues derived directly from organisms or cultured in vitro. Various samples may be used for detection of the marker according to the present invention, but the present invention is not limited thereto. In one embodiment, the samples include hepatocytes and liver tissue, and the hepatocytes are either primary hepatocytes isolated directly from animals or established hepatocyte-derived cell lines, for example, hepatocyte-derived cell lines which are generally used in experiments, such as HepG2, and AML12. In other embodiments, whole blood, serum and/or plasma may be used. In another embodiment, a tissue or cell obtained from an organism having, suspected of having, or likely to develop a disease or an in-vitro cell culture may be used, but the present invention is not limited thereto. The biological sample also includes fractions or derivatives of the blood, cells, or tissues. In the case of using cells or tissues, the cells themselves or a lysate of the cells or tissues may be used.

As used herein, the detection includes quantitative and/or qualitative analysis, and includes detection with regard to presence or absence and detection of expression level. Such methods are known in the art, and those skilled in the art will select an appropriate method for the implementation of the present invention.

The marker according to the present invention can be detected through quantitative or qualitative analysis in terms of the presence or absence of nucleic acids, in particular, mRNA and/or proteins, and/or the expression level itself, change in expression level, and difference in expression level.

The detection of such a biomarker according to the present invention may be based on functional and/or antigenic characteristics of the marker. The marker according to the present invention may be detected using a substance that is capable of detecting the activity or function of the marker, or specifically interacts with a nucleic acid encoding a protein, in particular at the mRNA level and/or the protein level.

In this aspect, the detection reagent according to the present invention is a reagent capable of detecting the marker according to the present invention through quantitative or quantitative analysis in various ways at the protein or nucleic acid level.

Various methods for qualitatively or quantitatively detecting known nucleic acids and proteins may be used for quantitative and qualitative analysis of markers according to the present invention.

Qualitative or quantitative detection methods at the protein level include, for example, Western blot, ELISA, radioimmunoassay, immunodiffusion, immunoelectrophoresis, tissue immunostaining, immunoprecipitation assay, complement fixation assay, binding to labeled antibody in solution/suspension, detection using flow cytometry, detection using mass spectrometry, or detection using a protein array such as an antibody.

Alternatively, as a qualitative or quantitative detection method at the nucleic acid level, a method using a nucleic acid transcription and amplification system, an eTag system, a system based on labeled beads, an array system such as a nucleic acid array, etc. may be used.

Such a method is well-known and can be, for example, chip-based capillary electrophoresis (Colyer et al. 1997. J. Chromatogr. A. 781(1-2):271-6), mass spectroscopy (Petricoin et al. 2002. Lancet 359: 572-77), eTag systems (Chan-Hui et al. 2004. Clinical Immunology 111:162-174), or microparticle-enhanced nephelometric immunoassay (Montagne et al. 1992. Eur. J. Clin. Chem. Clin. Biochem. 30:217-22).

In one embodiment, a sandwich-type immunoassay such as ELISA (enzyme-linked immunosorbent assay) or RIA (radio immunoassay) may be used. In accordance with this method, a biological sample is added to a first antibody bound to a solid substrate, for example, beads, membranes, slides, or microtiter plates made of glass, plastic (e.g., polystyrene), polysaccharide, nylon, or nitrocellulose, and then the protein can be qualitatively or quantitatively detected by labeling with a label that enables direct or indirect detection, for example, a radioactive material such as 3H or 125I, a fluorescent material, a chemiluminescent material, hapten, biotin, digoxigenin, etc., or through binding of antibodies conjugated with enzymes such as horseradish peroxidase, alkaline phosphatase, and malate dehydrogenase that can develop color or emit light through interaction with a substrate.

In another embodiment, immunoelectrophoresis such as Ouchterlony plate, Western blot, Crossed IE, Rocket IE, Fused Rocket IE, or affinity IE, which can simply detect a marker through antigen-antibody binding, may be used. The immunoassay or immunostaining method is described in Enzyme Immunoassay, E. T. Maggio, ed., CRC Press, Boca Raton, Florida, 1980; Gaastra, W., Enzyme-linked immunosorbent assay (ELISA), in Methods in Molecular Biology, Vol. 1, Walker, J. M. ed., Humana Press, N J, 1984, etc. By analyzing the intensity of the final signal through the above-described immunoassay process, that is, by comparing signals with a normal sample, it is possible to diagnose whether or not a disease has occurred.

The reagents or substances used in these methods are known, and include, for example, an antibody, substrate, nucleic acid, or peptide aptamer that specifically binds to the marker, or a receptor, ligand, cofactor, or the like that specifically interacts with the marker. The reagent or material that specifically interacts with or binds to the marker of the present invention may be used in a chip method or in combination with nanoparticles.

In one embodiment, an antibody specifically recognizing ITIH1 is used as a detection substance.

As used herein, the term "antibody" refers to a protein that binds to another molecule (antigen) through the variable regions of light and heavy chains, and includes IgG, IgD, IgA, and IgE types. Antibodies include polyclonal antibodies, monoclonal antibodies, and multispecific antibodies. In addition, the antibody of the present invention includes monoclonal antibodies having various types of structures, for example, an intact antibody (intact Ab) including two full-length heavy chains and two full-length light chains, and a fragment thereof, a chimeric antibody, a human antibody, a humanized antibody, or another genetically engineered antibody having characteristics according to the present invention, which includes or does not include a constant region.

As used herein, the term "antigen-binding fragment" refers to a part of the intact antibody described above, and is a sequence having one or more sequences shorter than the amino acid sequence of the intact antibody in length. In terms of functionality, the antigen-binding fragment includes at least a part of the activity or function of the intact antibody or parent antibody, and examples thereof include, but are not limited to, Fab (fragment for antigen binding), Fab', F(ab')$_2$, Fv or single-chain antibody (SCA, e.g., scFv or dsFv), bispecific scFv, and diabodies.

The antibodies according to the present invention include antigen-binding fragments, variants, and derivatives thereof, and include, but are not limited to, polyclonal, monoclonal, multispecific, human, humanized, primatized, or chimeric antibodies, single-chain antibodies, and epitope-binding fragments, for example, Fab, Fab', F(ab')$_2$, F(ab)$_2$, Fd, Fvs, single-chain Fvs (scFV), disulfide-linked Fvs (sdFv), and fragments including a VL or VH region. The antibody according to the invention may be of any type, for example IgG, IgE, IgM, IgD, IgA or IgY, and may also be of any class, for example IgG1, IgG2, IgG3, IgG4, IgA1, or IgA2, or a subclass thereof.

The antibody or antibody fragment of the present invention may be a chimeric antibody. As used herein, the term "chimeric antibody" refers to an antibody that includes at least a part of a variable region, that is, an antigen-binding site and a constant region (including CL1 for the light chain, and CH1, CH2, and CH3 for the heavy chain) of the antibody derived from different species. For example, the variable region may be derived from a mouse, and the constant region may be derived from a human. Alternately, the antibody means a class-switched antibody, for example an antibody switched from an IgG type to an IgE type. Chimeric antibodies are typically produced through recombinant DNA techniques, and reference may be made to, for example, Morrison et al. PNAS USA 81 (1984) 6851-6885; and U.S. Pat. No. 5,202,238.

The antibody or antibody fragment of the present invention may be a humanized antibody. As used herein, the term "humanized antibody" means an antibody that has a human antibody as a framework and a portion of the CDR region which has been modified to include only a portion essential for specifically binding to an antigen, among the CDRs of the species from which the antibody molecule is originally derived. For example, among the CDRs of the antibody derived from a monkey or mouse, the remaining CDR regions and light- and heavy-chain frameworks excluding regions essential for specific binding to an antigen are replaced with human antibodies. Production methods are described, for example, in Riechmann et al. (1988) Nature 332:323-327.

The antibody or antibody fragment of the present invention may be a polyclonal or monoclonal antibody. The monoclonal antibody is basically prepared through fusion of myeloma cells with splenocytes derived from immunized mammals, and may be prepared by various methods known in the art.

Furthermore, the antibody, antigen-binding fragment, variant, or derivative thereof according to the present invention may be conjugated to a functional substance such as a therapeutic agent, prodrug, peptide, protein, enzyme, virus, lipid, biological response modifier, or PEG (polyethylene glycol) for various purposes. Depending on the type of the material to be conjugated therewith, it may be prepared using various methods. Reference may be made, for example, to the following literature: Amon et al. "Monoclonal Antibodies For Immunotargeting Of Drugs In Cancer Therapy", in Monoclonal Antibodies And Cancer Therapy, Reisfeld et al. (eds.), pp. 243-56 (Alan R. Liss, Inc. (1985); Hellstrom et al. "Antibodies For Drug Delivery", in Controlled Drug Delivery (2nd Ed.), Robinson et al. (eds.), Marcel Dekker, Inc., pp. 623-53 (1987).

Fragments of antibodies can be obtained by treatment with pepsin or papain. The F(ab')$_2$ fragment can be obtained by treating an intact antibody with pepsin, which is subsequently treated with a thiol reducing agent to obtain a Fab fragment including part of a light chain and a heavy chain. The Fab fragment may also be obtained by treating an intact antibody with papain. For example, by treating the antibody produced from the hybridoma of the present invention with pepsin or papain, an antibody fragment that specifically recognizes ITIH1 such as F(ab')2 or Fab can be prepared.

The Fv fragment is an antibody fragment composed only of the variable regions of the heavy and light chains, and the two variable regions can be linked by non-covalent or covalent bonds such as chemical crosslinking agents or intermolecular disulfide bonds (Inbar et al. (1972) PNAS 69:2659-2662). For example, the Fv fragment may be prepared by treating the antibody produced from the hybridoma of the present invention with an enzyme to isolate only the variable regions of the heavy and light chains, or using recombinant DNA technology.

The SCA fragment may be produced by enzyme treatment or genetic engineering, and is an antibody fragment in which the variable region of the light chain is linked to the variable region of the heavy chain by a linker such as a polypeptide. For the method of producing ScFv, reference may be made, for example, to those described in U.S. Pat. No. 4,936,778 or 5,892,019, and the antibody may be produced by treating the antibody produced in the hybridoma according to the present invention with an enzyme or using recombinant DNA technology, for example, producing a vector including a nucleic acid sequence encoding the heavy-chain and/or light-chain variable region of the antibody, and expressing the same in appropriate cells.

As used herein, the term "binding" or "specific binding" refers to the affinity of an antibody or antibody composition of the present invention for an antigen. The term "specific binding" in the antigen-antibody binding may be distinguished from non-specific background binding, typically when the dissociation constant (Kd) is less than $1\times10^{-5}$ M, less than $1\times10^{-6}$ M, or less than $1\times10^{-7}$ M. The specific binding can be detected using a method known in the art, for example, ELISA, surface plasmon resonance (SPR), immunoprecipitation, or coprecipitation, and an appropriate control group that can differentiate the specific binding from the non-specific binding may be present.

The antibody clone 5D6 prepared in one embodiment according to the present invention has a dissociation constant of $2.43\times10^{-10}$ M, and the other antibody clone 9E1 has a dissociation constant $1.33\times10^{-10}$ M, indicating high affinity for ITIH1.

In one embodiment, the antibody or antigen-binding fragment specifically recognizing the ITIH1 includes a light-chain variable region including the complementarity-determining regions CDRL1, CDRL2, and CDRL3 set forth in SEQ ID NOS: 1, 2, and 3, respectively, and a heavy-chain variable region including the complementarity-determining regions CDRH1, CDRH2, and CDRH3 set forth in SEQ ID NOS: 4, 5, and 6, respectively, or a light-chain variable region including the complementarity-determining regions CDRL1, CDRL2, and CDRL3 set forth in SEQ ID NOS: 7, 8, and 9, respectively, and a heavy-chain variable region including the complementarity-determining regions CDRH1, CDRH2, and CDRH3 set forth in SEQ ID NOS: 10, 11, and 12, respectively.

In another embodiment, the antibody includes a light-chain variable region set forth in SEQ ID NO: 13 and a heavy-chain variable region set forth in SEQ ID NO: 14; or a light-chain variable region set forth in SEQ ID NO: 15 and a heavy-chain variable region set forth in SEQ ID NO: 16.

In another embodiment, the antibody may be an antibody or antigen-binding fragment that specifically recognizes ITIH1, which is a monoclonal antibody, a chimeric antibody, a humanized antibody, or a human antibody.

In another embodiment, the epitope of ITIH1 recognized by the antibody includes at least one of polypeptides set forth in SEQ ID NO: 17, SEQ ID NO: 18, SEQ ID NO: 19, SEQ ID NO: 20, or SEQ ID NO: 21 for the antibody including the light-chain variable region including the complementarity-determining regions CDRL1, CDRL2, and CDRL3 set forth in SEQ ID NOS: 1, 2, and 3, respectively, and the heavy-chain variable region including the complementarity-determining regions CDRH1, CDRH2, and CDRH3 set forth in SEQ ID NOS: 4, 5, and 6, respectively, or the antibody including the light-chain variable region set forth in SEQ ID NO: 13 and the heavy-chain variable region set forth in SEQ ID NO: 14, and the epitope of ITIH1 recognized by the antibody includes at least one of polypeptides set forth in SEQ ID NO: 22 or SEQ ID NO: 23 for the antibody including the light-chain variable region including the complementarity-determining regions CDRL1, CDRL2, and CDRL3 set forth in SEQ ID NOS: 7, 8, and 9, respectively, and the heavy-chain variable region including the complementarity-determining regions CDRH1, CDRH2 and CDRH3 set forth in SEQ ID NOS: 10, 11, and 12, respectively, or the antibody including the light-chain variable region set forth in SEQ ID NO: 15, and the heavy-chain variable region set forth in SEQ ID NO: 16.

The marker used herein can also be detected quantitatively and/or qualitatively using a variety of known methods at the level of nucleic acids, particularly at the level of mRNA.

Qualitative or quantitative detection methods at the nucleic acid level include, for example, reverse transcription polymerase chain reaction (RT-PCR)/polymerase chain reaction, competitive RT-PCR, real-time RT-PCR, nuclease protection assay (NPA), for example, RNase, S1 nuclease assay, in-situ hybridization, DNA microarray or chip or Northern blot, etc. for detection at the mRNA level, detection of expression level, or detection of patterns, and these assay methods are known and may be performed using commercially available kits, and those skilled in the art will be able to select the appropriate methods to implement the present invention. For example, Northern blot may be used to determine the size of transcripts present in cells and has an advantage of using various probes, NPA is useful for multi-marker analysis, in-situ hybridization makes it easy to determine the position of transcripts in cells or tissue, and reverse transcription polymerase chain reaction is useful for performing detection a small amount of a sample. In addition, a binding agent that specifically binds to a nucleic acid such as mRNA or cRNA derived from a gene encoding the biomarker protein according to the present invention or an array including the binding agent may be used.

The reagent or material used in the method for detecting the biomarker at the nucleic acid level is of a known type. For example, in a method for determining the presence or absence of mRNA and the amount thereof using RT-PCR, a detection reagent includes a polymerase and probes and/or primer pairs specific for the mRNA of the marker of the present invention. The term "primer" or "probe" means a nucleic acid sequence having a free 3' hydroxyl group capable of complementarily binding to a template and allowing reverse transcriptase or DNA polymerase to initiate replication of the template. The detection reagent used herein may be labeled with a chromogenic, luminescent, or fluorescent substance as described above for signal detection. In one embodiment, Northern blot or reverse transcription PCR (polymerase chain reaction) is used for mRNA detection. The latter case involves detecting a specific gene from a sample using a specific primer or a combination of a primer and a probe after isolating the RNA of the sample, particularly mRNA, and synthesizing cDNA therefrom, and is capable of determining the presence/absence of the specific gene or the expression level. Such methods are described, for example, in the literature (Han, H. et al, 2002. Cancer Res. 62: 2890-6).

In another aspect, the present invention is directed to a kit for diagnosing a disease accompanied by impaired glucose tolerance in a subject, the kit containing a reagent for detecting the ITIH1 marker.

The detection reagent included in the kit according to the present invention is as described above and the kit may further include a user guideline.

In another aspect, the present invention is directed to a method for quantitatively and/or qualitatively detecting an ITIH1 biomarker at a nucleic acid and/or protein level from a biological sample derived from a subject in vitro for the diagnosis or prognosis of a disease accompanied by impaired glucose tolerance.

In one embodiment, the present invention provides a method for detecting an ITIH1 biomarker in order to provide information necessary for the diagnosis or prognosis of a disease accompanied by impaired glucose tolerance, wherein the method includes detecting the presence and/or concentration of nucleic acid and/or protein of the ITIH1 biomarker from a biological sample derived from a test subject; comparing the result of detection for the concentration or presence of the nucleic acid, particularly mRNA, or protein with the result for the corresponding marker in a normal control sample, and determining that there occurs a disease accompanied by impaired glucose tolerance when there is a change in the concentration of nucleic acid or protein in the sample derived from the subject, or there is a change in the presence or absence of the nucleic acid or protein in the sample derived from the subject compared to the normal control sample.

In the method of the present invention, detection of the presence/absence or expression level of a marker may be determined at the protein and/or nucleic acid level, as described above.

The biological sample used in the method according to the present invention is as described above.

Detection of the marker for diagnosis of the disease accompanied by impaired glucose tolerance according to the method of the present invention may include both qualitative and quantitative detection, and the marker may serve as an indicator for the onset and progression of the disease, and may be used to detect the onset of the disease, progression of the disease, or for diagnosis or prognosis of the disease.

The method of the present invention may further include using non-protein clinical information of a patient, i.e., clinical information other than the marker, in addition to the result of marker analysis, in order to provide information on the diagnosis or prognosis of a disease accompanied by impaired glucose tolerance. Such non-protein clinical information includes, for example, the patient's age, gender, weight, diet, underlying disease, HbA1c (glycated hemoglobin), postprandial blood sugar, fasting blood sugar, blood insulin concentration, HOMA-IR, C-peptide concentration, adipose tissue IR, various lipid indicators (total cholesterol, triglyceride, free fatty acid), BMI (body mass index), and NAFLD activity scores (NAS score; steatosis grade, lobular inflammation, ballooning).

The method of the present invention includes linking the result of detection of the marker with the diagnosis or prognosis of a disease accompanied by impaired glucose tolerance, wherein the linking includes diagnosis based on comparison between the result of determination of protein amount or presence, or nucleic acid amount or presence, and the result of detection of the marker in the normal control group. Here, the ITIH1 protein is differentially expressed compared to the control group in a disease accompanied by impaired glucose tolerance, and provides information for diagnosis of the disease in the subject when the amount of ITIH1 is remarkably reduced or absent compared to the result of detection for the control group. In another embodiment of the present invention, the linking includes linking a sample of a normal control to a subject, setting a threshold value of each marker for diagnosing whether or not a disease occurs, and comparing the result of detection for the subject with the threshold value.

Hereinafter, the present invention will be described in more detail with reference to the following examples. These examples are provided merely for illustration of the present invention, and should not be construed as limiting the scope of the present invention.

EXAMPLE

Test Method
Animal Test

All animal experiments were performed in accordance with animal experimentation guidelines established by Seoul National University. Animals were kept under an environment of alternating light and dark at a 12-hour cycle, and were bred with free access to feed. In all experiments, male C57BL/6 strain mice were used. In the diet-induced obesity model experiment, 8-12 week old mice were fed a high-lipid diet (60% of the intake of dietary calories derived from lipids) or a normal diet for 5 weeks. In the glucose oral administration model experiment, 10-week-old C57BL/6 mice were fasted overnight, orally administered with glucose (2 g/kg body weight), and then euthanized at the indicated time, and samples were collected therefrom. For the production of Ga13-deficient mice, $Gna13^{flox/flox}$ mice (provided by Professor Stefan Offermanns of Max Planck Institute, Germany) were crossed with transgenic mice expressing the albumin-Cre gene (purchased from Jackson Laboratory) to construct liver-selective Gna13-deficient mice. $Gna13^{flox/flox}$, which does not express the Cre gene, was used as a control. In the diet-induced obesity model experiment, 8-12 week old mice were fed a high-lipid diet (60% of dietary calories consumed from lipids) or a normal diet for 5 weeks. In the glucose oral administration model experiment, 10-week-old C57BL/6 mice were fasted overnight, orally administered with glucose (2 g/kg body weight), and euthanized at the indicated time, and tissue samples were collected therefrom.

Western Blot

The same amount of protein for each sample was separated depending on the molecular weight by sodium dodecyl sulfate-polyacrylamide gel electrophoresis (SDS-PAGE) and transferred to a nitrocellulose membrane (GE healthcare). The membrane was reacted with a 5% skim milk solution for 1 hour, then reacted with a primary antibody recognizing each protein for at least 12 hours, and then further reacted with HRP-conjugated IgG (Zymed Laboratories) for one hour, and color development was induced using Amersham ECL western blotting detection reagent (GE Healthcare).

Injection of Plasmid into Mice Using Hydrodynamic Injection

A large amount of shRNA (shOGT) or control plasmid (shCon) targeting OGT was obtained, dissolved in PBS in an amount of volume corresponding to 8% of the mouse weight, and then injected into the tail of 8-week-old normal or hepatocyte-selective Gna13-deficient mice. Each mouse was injected with 25 μg of plasmid within 5 seconds.

Insulin Sensitivity Indicator (Akt Phosphorylation) Experiment

Primary hepatocytes were isolated from livers of normal or Ga13-deficient animals that had been fed a normal diet, and then conditioned media, obtained by treatment with ITIH1-targeting siRNA or a control group thereof, were cultured in 313-L1 and C2C12 cell lines, respectively, for 24 hours. Then, the result was treated with insulin (100 nM), a cell homogenate was sampled 15 minutes later, and the degree of Akt phosphorylation as a downstream signal of the insulin receptor was analyzed through an immunochemical method using a phospho-Akt antibody (Cell Signaling Technology, USA). Using the Akt antibody (Cell Signaling Technology, USA) that recognizes the total Akt protein, the expression level of phosphorylated Akt was calibrated based on the expression level of total Akt and quantified.

2-Deoxyglucose Absorption Capacity Test

The content of 2-deoxyglucose absorbed into cells was measured in the cell homogenate through an enzyme reuse amplification method using a kit for measuring glucose absorption capacity according to the manufacturer's instructions.

Glucose Tolerance Test

From the day before the glucose tolerance test, the mice were allowed to freely access drinking water while fasting for about 16 hours. The fasting blood glucose was measured (time 0), the mice were orally administered with glucose at a concentration of 2 g/kg body weight, and the blood glucose concentration was measured using a glucometer (an Accu-Chek active glucose detection apparatus, Roche) from a small amount of blood obtained by forming a small wound on the tail after 15 minutes, 30 minutes, 60 minutes, and 90 minutes had elapsed.

Insulin Tolerance Test

On the day of the insulin tolerance test, the mice were allowed to freely access drinking water while fasting for about 4 to 6 hours. Then, the fasting blood glucose was measured (time 0) and the mice were administered intraperitoneally with insulin at a concentration of 1.5 IU/kg body weight. Blood glucose concentration was measured using Glucometer (an Accu-Chek active glucose detection apparatus, Roche) from a small amount of blood obtained by forming a small wound on the tail whenever 30 minutes, 60 minutes, 90 minutes, and 120 minutes had elapsed.

Obtaining Conditioned Medium Samples from Primary Hepatocytes

Primary hepatocytes isolated from mice fed a high-lipid diet for 5 weeks were rinsed with PBS and then cultured using Opti-MEM medium from which serum was removed. Then, the conditioned medium obtained by performing culture for 24 hours was collected, mixed, and centrifuged at 3,000 g for 5 minutes, and the supernatant was collected and stored in a freezer at −80° C. until used in the experiment. For secretome analysis, large amounts of serum proteins (albumin and immunoglobulin) in the conditioned medium were removed using a commercially available immuno-neutralizing adsorbent resin, followed by concentration through centrifugation at 4,800 g at 4° C. for 90 minutes using an Amicon ultra tube.

Preparation of Hepatocyte Conditioned Medium Samples for Proteomics Analysis

In order to use the conditioned medium sample obtained from primary hepatocytes for liquid chromatography-mass spectrometry, the protein concentration of the conditioned medium was measured using Quick Start™ Bradford 1× dye reagent. Then, the protein fraction (100 mg) was dissolved in 50 mM ammonium bicarbonate and then reduced/alkylated using each of dithiothreitol and iodoacetamide. To lyse the sample by enzymatic reaction, protein and trypsin enzyme were added at a ratio of 50:1 and reacted at 37° C. for 16 hours. The sample subjected to the enzymatic reaction was allowed to flow down in a high-pH liquid phase in a C18 column and divided into 12 fractions.

LC-MS/MS Analysis for Hepatocyte Secretome Analysis

Spectral raw data were obtained using a linear trap quadrupole (LTQ)-Orbitrap (Thermo Fisher, San Jose, CA) equipped with an EASY-nLC II (Thermo Fisher Scientific). Using an autosampler, a total of 6 ml of the peptide solution was loaded on an EASY-column: C18 trap-column of i.d. 100 mm, length 20 mm, and particle size of 5 mm (Thermo Scientific). The peptides were desalted and concentrated in a trap column for 15 minutes at a flow rate of 2 ml/min. Then, the trapped peptide was isolated in an EASY-column: a C18 analytic-column of i.d. 75 mm, 100 mm length, and 3 mm particle size (120 Å from Thermo Scientific). The mobile phase consisted of 100% water (A) and 100% acetonitrile (ACN) (B), each containing 0.1% formic acid. A voltage was applied to produce an electrospray of 2.0 kV. During the chromatographic separation process, the LTQ-Orbitrap was operated in a result-independent acquisition mode. Previously fragmented ions were removed for 180 seconds. Datasets generated with LTQ-Orbitrap were analyzed using a proteome discoverer (version 1.3.0.339, Thermo Fisher Scientific) and a scaffold (version 4.4.1, Proteome Software Inc., Portland, OR) platform, and then the UniProt mouse protein database (release 2014 June) was searched using SEQUEST and X! tandem. Peptide identification was used when the probability exceeded 90% or 95% in the scaffold local FDR algorithm. In addition, when at least two unique peptides were included, the identified peptides were used. Protein probability was determined using protein prophet algorithm. Secretory proteins may be defined as containing a signal peptide at the N-terminus, or being distributed outside cells in terms of the cellular compartment with reference to the UniProt database (gene ontology (GO:0005615 or GO:0005576), or may be defined as being "secreted" outside the cells. The term "liver-enriched protein" corresponds to the case in which "liver tissue-enriched" or "liver-tissue-selective" proteins are defined in the UniProt or human protein atlas database.

Production and Characterization of ITIH1 Monoclonal Antibody

Monoclonal antibodies 5D6 and 9E1 against ITIH1 were produced by AbClon Inc. (Seoul, Korea). In brief, human ITIH-1 antigen (SEQ ID NO: 24) produced in HEK293F was purified, 100 to 200 μg of the human ITIH-1 antigen was mixed with an adjuvant (Sigma), the resulting mixture was injected into mice (BALB/c), and blood was collected from mice to determine whether or not antibodies were produced by ELISA. After immunization was performed 2 times, the antibody titer (1:5,000) increased appropriately. Then, the spleen was removed from the immunized mice, and B lymphocytes were isolated therefrom and were then fused with cultured myeloma cells (sp2/0). The fused cells were cultured in a medium supplemented with hypoxanthine, aminopterin, and thymidine (HAT medium), and only cells (hybridoma) fused with myeloma and B lymphocytes were selected and cultured (because B lymphocytes are normal cells and thus die during long-term culture, but myeloma cells are transformed cells and are thus eliminated by HAT selection). Among the obtained hybridoma cells, cells capable of producing an antibody that reacts with an antigen were identified by ELISA. At this time, a process of separating positive cells from negative cells using a limiting dilution method was repeatedly performed on cells that are positive for ELISA (cloning) to produce monoclonal cells (hybridoma) that produce antigen-reactive antibodies. The produced hybridoma cells were stored in a frozen state ($1 \times 10^6$ cell/ml).

The epitopes of 5D6 and 9E1 clonal antibodies were determined using the PEPperMAP® epitope mapping kit from AbClon Inc. in accordance with the manufacturer's instructions.

5D6 and 9E1 were bound to ITIH1 with high affinity, as shown in the table below, and affinity was determined by AbClon Inc. using an AR2G (Bio-Sensor). The results are as follows.

| Ligand | Kon (1/Ms) | Kdis (1/s) | Rmax (nm) | KD (M) | Full $X^2$ | Full $R^2$ |
|---|---|---|---|---|---|---|
| 5D6 | 2.91E+05 | 7.05E−05 | 0.3256 | 2.43E−10 | 0.0186 | 0.9968 |
| 9E1 | 3.34E+05 | 4.45E−05 | 0.9495 | 1.33E−10 | 0.0208 | 0.9996 |

Statistical Analysis

Protein bands visualized by immunochemical analysis were quantified using ImageJ software. Data were expressed as mean±standard error, and statistical significance between groups was classified as P<0.05 or P<0.01 using a Student's t-test. The multiple means comparison was performed using ANOVA, followed by the Bonferroni method to calculate statistical significance.

Example 1. Establishment of System Mimicking Hyperglycemia Stimulation Using Hepatocytes Derived from Liver-Selective Ga13 (Upstream Regulator of ITIH1)-Deficient Mice In the present invention, primarily cultured hepatocytes were isolated from liver-selective Ga13 (upstream regulator of ITIH1)-deficient mice and were then cultured for 12 hours in a culture medium containing a low concentration (euglycemia) or a high concentration (hyperglycemia) of glucose to devise a cell-based assay mimicking hyperglycemic stimulation (FIG. 1). At this time, the O-GlcNAc modification (CTD110.6 clone) showing increased activity in a hyperglycemic environment was increased by stimulation with high-concentration glucose compared to stimulation with low-concentration glucose, and the expression of ITIH1, a key target, was remarkably increased. These results indicate that a cell-based assay that mimics a high blood glucose situation in a living organism was successfully established, which indicates that this test method can be used to determine the efficacy of small molecule compound candidates targeting ITIH1.

Example 2. Establishment of Animal Model System in which Ga13 (Upstream Regulator of ITIH1) is Selectively Deficient in the Liver Based on the result showing that Ga13 expression is reduced in a hepatocyte-selective manner in various hyperglycemic conditions (FIG. 3), hepatocellular-selective Ga13-deficient animals having a condition similar to hyperglycemia (or impaired glucose tolerance) were constructed.

An experimental animal model for verifying the efficacy of a substance used in the cell-based assay proposed herein was suggested. In this example, after single application of acute hyperglycemic stimulation, ITIH1 production and changes in secretion thereof were observed. The results are shown in FIG. 2. 6 hours after oral administration (2 g/kg) of glucose to normal mice or Ga13-deficient mice (Ga13LKO), the content of ITIH1 in the liver tissue and serum was measured. Similar to the results of the primary hepatocyte culture experiment suggested in FIG. 1, upon application of glucose stimulation, the content of ITIH1 in the liver tissue and blood of mice increased and the expression of ITIH1 increased in Ga13 gene-deficient mice compared to normal mice, even in the absence of glucose stimulation. When glucose stimulation was applied thereto, the ITIH1 content was very high. This is an animal test method using an ITIH1 target proposed in the present invention, which is effective and remarkably improved compared to a conventional model to which a high-lipid diet is administered for 12 to 16 weeks.

Example 3. Correlation of Changes in Liver Ga13 Expression with Blood Glucose in Various Hyperglycemic Animal Models In this invention, it was found that the expression of Ga13, which was identified as an upstream regulator of ITIH1, was reduced in the liver tissue of a hyperglycemic experimental animal model induced with a high-lipid diet (left) and a genetically modified mouse model induced with hyperglycemia and obesity (right) (FIG. 3A). The decrease in Ga13 expression in liver tissue was analyzed using immunoblot analysis when C57BL/6 mice were fed a high-fat diet configured such that 60% of all calories consumed were derived from lipids for 9 weeks. There was no change in Ga13 expression in adipose tissue or skeletal muscle isolated from the same mouse (left). In addition, in liver tissue of a transgenic mouse model lacking an appetite-suppressing center, the expression of Ga13 was remarkably decreased in hyperglycemia-induced mice (obob, dbdb) compared to normal mice. Pearson correlation analysis was performed to analyze the relationship between decreased liver Ga13 expression and hyperglycemia in various diabetes models using experimental animals. As a result, hepatic Ga13 expression and blood glucose showed a remarkably high correlation in all hyperglycemia models (FIG. 3B). These results indicate that the expression of Ga13 in the liver is reduced in multiple conditions accompanied by hyperglycemia and is directly correlated with hyperglycemia.

Example 4. Increased ITIH1 Concomitant with Hepatic Ga13 Expression Decrease in Hyperglycemic Animal Model Example 4-1. Reduction of Ga13 Expression in Hyperglycemic Animal Model In this example, a hyperglycemia experimental animal model induced as a type 1 diabetes-like model was constructed and the expression changes of Ga13 and ITIH1 suggested in the present invention were observed. In the present invention, streptozotocin was administered intraperitoneally to 10-week-old C57BL/6 mice at a dose of 50 mg/kg (citrate buffer, pH 4.5) once a day for a total of 5 consecutive days. After 4 weeks, the mice were euthanized to obtain a sample. As a result, the expression of Ga13, an upstream regulator of ITIH1, was decreased, similar to other hyperglycemia models, and the expression of ITIH1 was remarkably increased (FIG. 3C, left). The statistical significance was also verified through Pearson correlation analysis between liver Ga13 expression and blood sugar (FIG. 3C, right). This suggests that the expression of ITIH1 increased along with the decrease in liver Ga13 expression in various hyperglycemic animal models accompanied by diabetes and that this increased ITIH1 expression has a strong negative correlation with actual blood glucose.

Figure 4B:
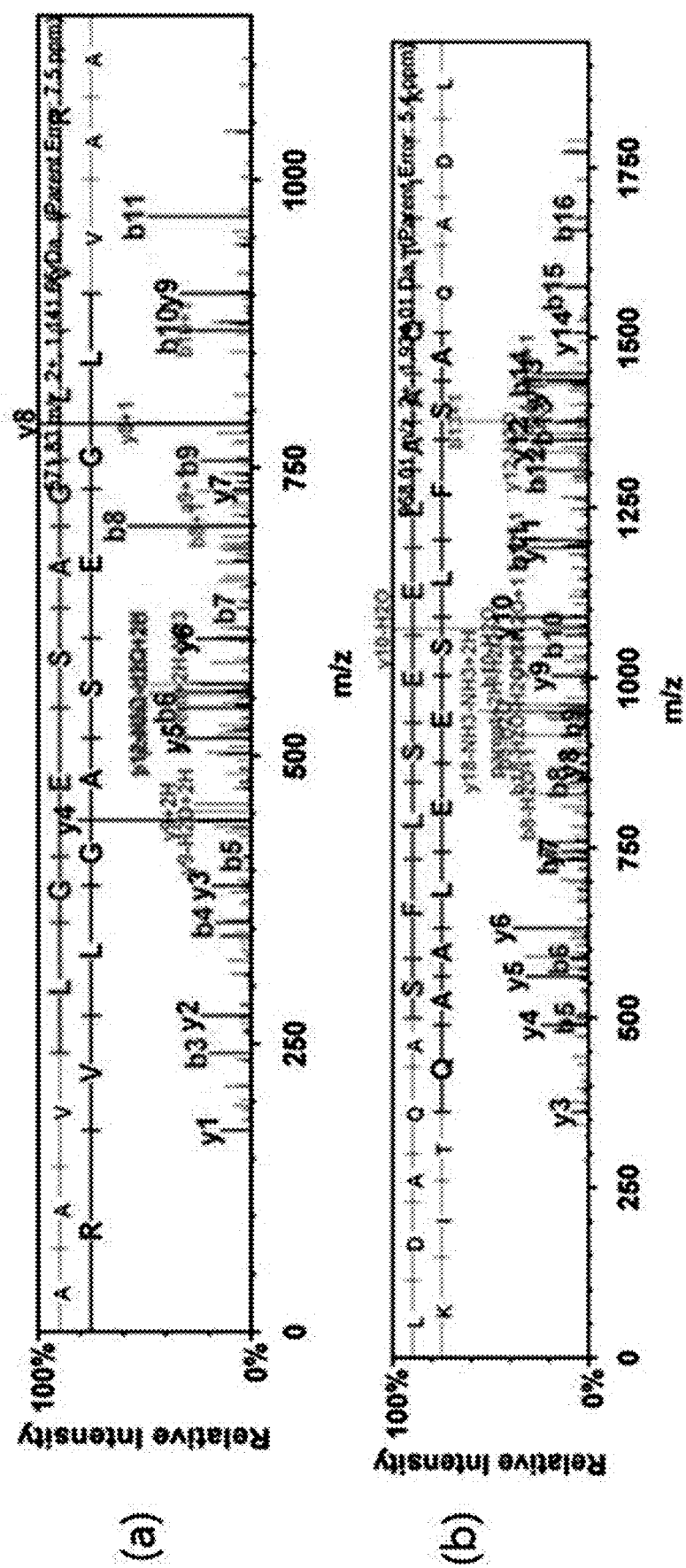

Example 4-2. LC-MS Analysis Revealed Protein ITIH1 with Large Protein Expression Change in Ga13-Deficient Liver In order to identify novel proteins that are secreted from Ga13-deficient liver and induce glucose intolerance, a conditioned medium obtained by culturing primary hepatocytes of liver Ga13-deficient mice was concentrated, and proteins contained in the samples were analyzed using mass spectrometry. After isolation of primary hepatocytes from normal mice and liver-selective Ga13-deficient mice that had been fed a high-lipid diet for 5 weeks, a conditioned medium obtained by culturing the primary hepatocytes in a medium devoid of fetal bovine serum for 24 hours was concentrated. Then, albumin and immunoglobulin present in large amounts in the conditioned medium were removed by adsorption on a commercially available resin, and the resulting sample was assayed using liquid chromatography-mass spectrometry. As a result, as shown in FIG. 4, from among the secured candidate proteins, proteins that were quantitatively two or more times changed in the hepatic Ga13-deficient group compared to the normal group were observed. ITIH1 was identified as the protein exhibiting the second largest change (increase). A plasma protease C1 inhibitor, which exhibits a greater increase, was excluded because the link was not clear in terms of correlation with diabetes and a previously reported result showed a function opposite that of the hepatic Ga13-deficient mouse with regard to inflammation.

Example 5. Identification of Mechanism by which Increase in OGT Resulting from Decrease in Ga13 in Hyperglycemic State Increases Stability of ITIH1

Ga13-selective hepatocyte-deficient mice were constructed, glucose tolerance and insulin tolerance tests were performed on mice that had been fed a high-lipid diet for 9 to 13 weeks, and the results are shown in FIG. 5. In the mice that had been fed a high-lipid diet, fasting blood glucose was significantly increased in hepatocyte-selective Ga13-deficient mice compared to normal mice (left). Additionally, when the glucose tolerance test (middle) and the insulin tolerance test (right) were performed, it was found that Ga13-deficient mice had lower glucose metabolism capability compared to normal mice.

The expression of ITIH1 in liver tissue and sera of normal or hepatocyte-selective Ga13-deficient mice fed a high-lipid diet was analyzed using an immunochemical method. The results are shown in FIG. 6. It can be seen therefrom that the expression of ITIH1 was remarkably increased in the livers and sera of Ga13-deficient mice compared to normal mice.

Liver samples were obtained 6 hours after oral administration of high-concentration glucose (2 g/kg body weight) to normal or hepatocyte-selective Ga13-deficient mice, and the expression of the corresponding targets was analyzed using an immunochemical method. The results are shown in FIG. 7. When a high concentration of glucose was administered to normal mice, Ga13 decreased, but the expression of ITIH1 and OGT increased, and expression thereof significantly increased in the livers of Ga13-deficient mice.

The invention claimed is:

1. A composition for detecting insulin resistance in a disease accompanied by impaired glucose tolerance, the composition comprising a substance for detecting an inter-alpha trypsin inhibitor heavy chain 1 (ITIH1),
   wherein the substance for detecting is an antibody or an antigen-binding fragment thereof, which specifically recognizes the ITIH1, and
   the antibody or the antigen-binding fragment thereof comprises:
   a light-chain variable region comprising complementarity-determining regions CDRL1, CDRL2, and CDRL3 set forth in SEQ ID NOS: 1, 2, and 3, respectively, and a heavy-chain variable region comprising complementarity-determining regions CDRH1, CDRH2, and CDRH3 set forth in SEQ ID NOS: 4, 5, and 6, respectively; or
   a light-chain variable region comprising complementarity-determining regions CDRL1, CDRL2, and CDRL3 set forth in SEQ ID NOS: 7, 8, and 9, respectively, and a heavy-chain variable region comprising complementarity-determining regions CDRH1, CDRH2, and CDRH3 set forth in SEQ ID NOS: 10, 11, and 12, respectively.

2. The composition according to claim 1, wherein the antibody or the antigen-binding fragment thereof comprises:
   a light-chain variable region set forth in SEQ ID NO: 13 and a heavy-chain variable region set forth in SEQ ID NO: 14; or
   a light-chain variable region set forth in SEQ ID NO: 15 and a heavy-chain variable region set forth in SEQ ID NO: 16.

3. The composition according to claim 1, wherein the antibody or the antigen-binding fragment thereof is a monoclonal antibody, a chimeric antibody, a humanized antibody, or a human antibody.

4. The composition according to claim 1, wherein
   an epitope of ITIH1 recognized by the antibody or the antigen-binding fragment thereof comprises at least one of polypeptides set forth in SEQ ID NO: 17, SEQ ID NO: 18, SEQ ID NO: 19, SEQ ID NO: 20, or SEQ ID NO: 21, for the antibody or the antigen-binding fragment thereof comprising the light-chain variable region comprising complementarity-determining regions CDRL1, CDRL2, and CDRL3 set forth in SEQ ID NOS: 1, 2, and 3, respectively, and the heavy-chain variable region comprising complementarity-determining regions CDRH1, CDRH2, and CDRH3 set forth in SEQ ID NOS: 4, 5, and 6, respectively, and
   the epitope of ITIH1 recognized by the antibody or the antigen-binding fragment thereof comprises at least one of polypeptides set forth in SEQ ID NO: 22 or SEQ ID NO: 23 for the antibody or the antigen-binding fragment thereof comprising the light-chain variable region comprising complementarity-determining regions CDRL1, CDRL2, and CDRL3 set forth in SEQ ID NOS: 7, 8, and 9, respectively, and the heavy-chain variable region comprising complementarity-determining regions CDRH1, CDRH2 and CDRH3 set forth in SEQ ID NOS: 10, 11, and 12, respectively.

5. The composition according to claim 2, wherein
   the epitope of ITIH1 recognized by the antibody or the antigen-binding fragment thereof comprises at least one of polypeptides set forth in SEQ ID NO: 17, SEQ ID NO: 18, SEQ ID NO: 19, SEQ ID NO: 20, or SEQ ID NO: 21 for the antibody or the antigen-binding fragment thereof comprising the light-chain variable region set forth in SEQ ID NO: 13 and the heavy-chain variable region set forth in SEQ ID NO: 14, and the epitope of ITIH1 recognized by the antibody or the antigen-binding fragment thereof comprises at least one of polypeptides set forth in SEQ ID NO: 22 or SEQ ID NO: 23 for the antibody comprising the light-chain variable region set forth in SEQ ID NO: 15 and the heavy-chain variable region set forth in SEQ ID NO: 16.

6. The composition according to claim 1, wherein the antibody or the antigen-binding fragment thereof specifically recognizes human or mouse-derived ITIH1.

7. The composition according to claim 1, wherein the composition is used for western blot, ELISA, radioimmunoassay, immunodiffusion, immunoelectrophoresis, tissue immunostaining, immunoprecipitation assay, complement fixation assay, FACS, mass spectrometry, or protein microarray.

8. A kit for diagnosing diseases accompanied by impaired glucose tolerance, the kit comprising the composition according to claim 1.

9. A method for detecting an ITIH1 biomarker, the method comprising:
detecting presence and/or a concentration of a protein of the ITIH1 biomarker from a biological sample derived from a test subject in order to provide information necessary for diagnosis or prognosis of a disease accompanied by impaired glucose tolerance;
comparing a result of detection for the presence and/or concentration of the protein with a result for a corresponding marker in a normal control sample; and
determining that there is a disease accompanied by impaired glucose tolerance when, compared to the normal control sample, there is a change in the concentration of protein in the sample derived from the subject, or there is a change with regard to presence or absence of the protein,
wherein the detecting the presence and/or concentration of the protein is performed using an antibody or the antigen-binding fragment thereof, and
the antibody or the antigen-binding fragment thereof comprises:
a light-chain variable region comprising complementarity-determining regions CDRL1, CDRL2, and CDRL3 set forth in SEQ ID NOS: 1, 2, and 3, respectively, and a heavy-chain variable region comprising complementarity-determining regions CDRH1, CDRH2, and CDRH3 set forth in SEQ ID NOS: 4, 5, and 6, respectively; or
a light-chain variable region comprising complementarity-determining regions CDRL1, CDRL2, and CDRL3 set forth in SEQ ID NOS: 7, 8, and 9, respectively, and a heavy-chain variable region comprising complementarity-determining regions CDRH1, CDRH2, and CDRH3 set forth in SEQ ID NOS: 10, 11, and 12, respectively.

10. The method according to claim 9, wherein the antibody or the antigen-binding fragment thereof comprises:
a light-chain variable region set forth in SEQ ID NO: 13 and a heavy-chain variable region set forth in SEQ ID NO: 14; or
a light-chain variable region set forth in SEQ ID NO: 15 and a heavy-chain variable region set forth in SEQ ID NO: 16.

11. The method according to claim 9, wherein the disease accompanied by impaired glucose tolerance comprises metabolic syndromes, type 1 diabetes mellitus, type 2 diabetes mellitus, diabetic nephropathy, inflammatory bowel diseases, obesity, hyperlipidemia, fat hepatitis, steatohepatitis, liver fibrosis or cirrhosis, kidney disease, muscle disease, or dementia.

12. The method according to claim 9, wherein the biological sample comprises serum, liver cells, or a liver tissue containing hepatocytes.

13. The method according to claim 9, wherein the comparing is performed using non-marker clinical information comprising HbA1c (glycated hemoglobin), postprandial blood glucose, fasting blood glucose, blood insulin concentration, HOMA-IR (homeostatic model assessment of insulin resistance), C-peptide concentration, adipose tissue insulin resistance, total cholesterol, triglyceride, free fatty acid, BMI (body mass index), NAS score (non-alcoholic fatty liver disease activity score), or a combination thereof.

14. The method according to claim 9, wherein the method using the antibody or the antigen-binding fragment thereof is western blot, ELISA, radioimmunoassay, immunodiffusion, immunoelectrophoresis, tissue immunostaining, immunoprecipitation assay, complement fixation assay, FACS, mass spectrometry, or protein microarray.

* * * * *